(12) United States Patent
Boozer et al.

(10) Patent No.: US 8,162,968 B2
(45) Date of Patent: Apr. 24, 2012

(54) LANCING DEVICE

(75) Inventors: Brad Boozer, Marblehead, MA (US); Joseph Flaherty, Westford, MA (US); Timothy Golnik, Boxford, MA (US)

(73) Assignee: Agamatrix, Inc., Salem, NH (US)

( * ) Notice: Subject to any disclaimer, the term of this patent is extended or adjusted under 35 U.S.C. 154(b) by 1063 days.

(21) Appl. No.: 11/733,032

(22) Filed: Apr. 9, 2007

(65) Prior Publication Data
US 2007/0239188 A1 Oct. 11, 2007

Related U.S. Application Data

(60) Provisional application No. 60/744,560, filed on Apr. 10, 2006.

(51) Int. Cl.
*A61B 17/32* (2006.01)

(52) U.S. Cl. ........ 606/182; 606/167; 606/181; 606/184; 606/185

(58) Field of Classification Search ................ 606/181, 606/182, 184; 600/136–139
See application file for complete search history.

(56) References Cited

U.S. PATENT DOCUMENTS

| | | | |
|---|---|---|---|
| 3,030,959 A * | 4/1962 | Grunert | 606/182 |
| 3,200,792 A * | 8/1965 | Zepell | 401/106 |
| 4,627,445 A | 12/1986 | Garcia et al. | |
| 4,790,678 A * | 12/1988 | Araki | 401/104 |
| 6,053,930 A | 4/2000 | Ruppert | |
| 6,192,891 B1 * | 2/2001 | Gravel et al. | 604/187 |
| 6,210,420 B1 * | 4/2001 | Mauze et al. | 606/182 |
| 6,479,618 B1 | 11/2002 | Vonderhagen | |
| 6,533,797 B1 * | 3/2003 | Stone et al. | 606/184 |
| 6,719,771 B1 | 4/2004 | Crossmann | |
| 6,729,785 B2 * | 5/2004 | Wijerama | 401/17 |
| 6,840,912 B2 | 1/2005 | Kloepfer et al. | |
| 6,852,119 B1 | 2/2005 | Abulhaj et al. | |
| 6,866,641 B2 | 3/2005 | Marshall | |
| 2003/0199912 A1 * | 10/2003 | Pugh | 606/182 |
| 2005/0265094 A1 | 12/2005 | Harding et al. | |
| 2006/0155210 A1 * | 7/2006 | Beckman et al. | 600/567 |
| 2006/0200181 A1 * | 9/2006 | Fukuzawa et al. | 606/181 |
| 2006/0241666 A1 * | 10/2006 | Briggs et al. | 606/181 |

FOREIGN PATENT DOCUMENTS
JP 2002-085384 A 3/2002
* cited by examiner

*Primary Examiner* — Gary Jackson
*Assistant Examiner* — Kevin Everage
(74) *Attorney, Agent, or Firm* — Larson & Anderson, LLC

(57) ABSTRACT

A lancing device is used with a lancet for lancing body tissue to result in a wound for bleeding. The lancing device has a cantilevered priming arm having a first arm portion that is generally parallel to an internal channel of the device and a second arm portion that is generally perpendicular to the internal channel. The second arm portion is connected to a lancet carrier and movement of the first arm portion toward the internal channel draws the lancet carrier to a primed position and stores energy in a lancet driver.

21 Claims, 23 Drawing Sheets

US 8,162,968 B2

LANCING DEVICE

CROSS-REFERENCE TO RELATED APPLICATIONS

The present application claims priority from and is a non-provisional application of U.S. provisional application Ser. No. 60/744,560 filed on Apr. 10, 2006 which is herein incorporated for all purposes by reference.

BACKGROUND

Lancing devices are typically used for the lancing of body tissue to result in a wound for bleeding. A blood sample then may be collected from the wound for measuring the concentration of an analyte such as glucose.

Currently available lancing devices, such as those disclosed in U.S. Pat. Nos. 6,053,930, 6,852,119, and 6,479,618 typically have a lancet carrier (including a lancet) and a spring loaded lancet driver mounted within a housing. On priming, the spring loaded lancet driver serves to store the energy required to propel the lancet carrier along the inside of the housing toward the skin of a user. The propulsion of the lancet causes the lancet to impact against and puncture the skin, causing a wound large enough for sampling blood. Such blood sampling is often painful and inconvenient.

Many users of such lancing devices suffer from physical impairments, such as arthritis, that prevent them from being able to adequately manipulate the priming means of the devices thereby failing to properly prime them. Such improper use of a lancet device often results in inadequate wound size for blood sampling and may require repeat lancing which causes more pain and multiple wounds. As a result, many patients may not be able to, or simply decide not to sample blood as frequently as suggested by their doctors in order to monitor their physiological functions adequately.

SUMMARY OF INVENTION

An improved lancing device is provided that is user-friendly and easy to use. The present invention provides a lancing device for use with a lancet for lancing body tissue to result in a wound for bleeding. In accordance with an embodiment of the present invention, the lancing device comprises:
(a) a housing having an internal channel extending within the housing from a first lancing end toward a second end of the housing;
(b) a lancet carrier translationally mounted within the internal channel for carrying a lancet along a strike path of the lancet carrier, said strike path starting at a primed position toward the second end of the housing and extending to a lanced position at the first lancing end of the housing,
(c) a lancet driver for storing energy and then driving the lancet carrier along the strike path from the primed position to the lanced position; and
(d) a first cantilevered priming arm comprising a first arm portion that is generally parallel to the internal channel and a second arm portion that is generally perpendicular to the internal channel, wherein the second arm portion is connected to the lancet carrier,
wherein movement of the first arm portion toward the internal channel draws the lancet carrier to a primed position and stores energy in the lancet driver.

DETAILED DESCRIPTION OF INVENTION

Figure 1A:
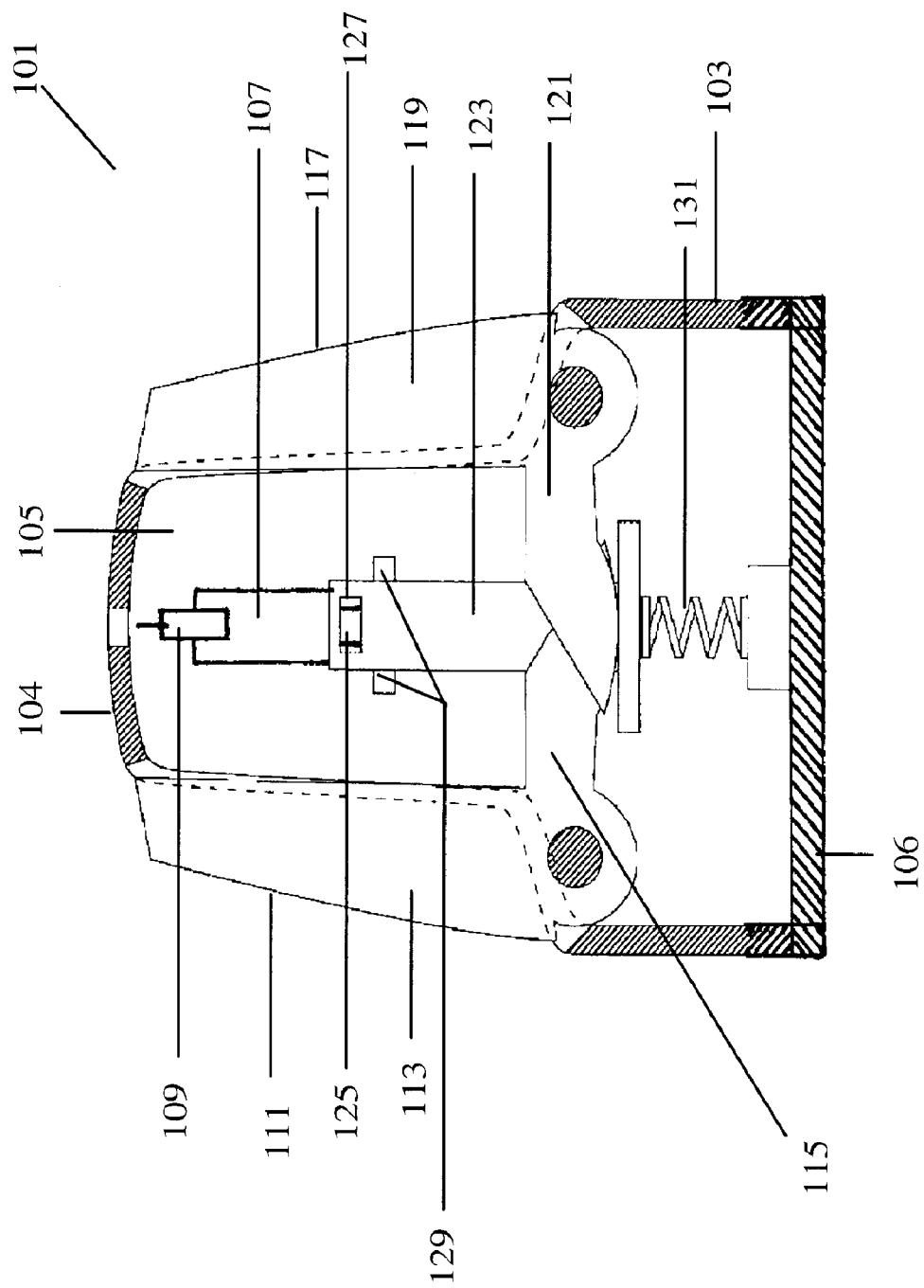
FIG. 1A is a cross-sectional top view of a lancing device in accordance with an embodiment of the present invention.

Lancing devices of the past including those disclosed in U.S. Pat. Nos. 6,053,930, 6,852,119, 6,479,618, and 6,210,420, all of which are herein incorporated by reference, typically have a lancet carrier (including a lancet) and a spring loaded lancet driver, mounted within a housing. As shown in FIG. 1C (FIG. 1 of U.S. Pat. No. 6,210,420) these lancet devices 1101 typically have a housing 1103 with an internal channel 1104, a lancet 1106 having a needle 1105 connected to a lancet carrier 1113, and a spring loaded lancet driver 1108 for driving the lancet carrier along the internal channel 1104 to the lancing end 1111 and bodily tissue 1112. The devices also have a priming means for priming the lancet device and storing energy in lancet driver 1108. In FIG. 1B the priming means is priming handle 1110. When a user pulls the handle 1110 along the internal channel 1104 and away from the lancing end 1111 of device 1101, the lancet carrier 1113 is locked into a primed position where energy is stored in spring 1108 (i.e. the lancet driver). When a user presses release button 1114, the energy stored in spring 1108 is released as the lancet carrier is driven along the internal channel 1104 toward the bodily tissue 1112 of a user. In one embodiment, the present invention provides an improved lancing device that is user friendly and easy to prime.

As described above with regard to FIG. 1C, lancing devices typically have a housing, an internal channel extending within the housing, a lancet carrier disposed in the internal channel, and a lancet driver. A user applies force to a housing to prime the lancet carrier which is then placed into a primed position. In one embodiment, the present invention provides an improvement to the lancing devices described above, the improvement comprises:

a cantilevered priming arm comprising a first arm portion that is generally parallel to the internal channel and a second arm portion that is generally perpendicular to the internal channel, wherein the second arm portion is connected to the lancet carrier, wherein movement of the first arm portion toward the internal channel draws the lancet carrier to a primed position and stores energy in the lancet driver.

The term "generally parallel" as it is used herein with reference to the first arm portion of the cantilevered priming arm(s) refers to the orientation of such with respect to the internal channel of the lancing device. At least part of the first arm portion is accessible by a user on the outside of the housing such that motion of the first arm portion toward the internal channel will be translated into priming motion of the lancet carrier along the strike path. In one embodiment the first arm portion will be disposed exactly parallel to the internal channel. In other embodiments, at resting position, the first arm portion will be tipped toward or away from the internal channel by up to 45 degrees, for example 40 degrees, 35 degrees, 30 degrees, 25 degrees, 20 degrees, 15 degrees, 10 degrees, or 5 degrees.

The term "generally perpendicular" as it is used herein with reference to the second arm portion of the cantilevered priming arm(s) refers to the orientation of such with respect to the internal channel of the device. Energy is translated from the movement of the first arm portion, around a pivot point, into movement of the second arm portion that draws the lancet carrier along the strike path toward a primed position. In a preferred embodiment, at resting position, the second arm portion is disposed exactly perpendicular (i.e. 90 degrees) to the internal channel. In another embodiment, at resting position, the second arm portion is disposed at a position that is 45 degrees away from perpendicular in either direction. For example 40 degrees, 35 degrees, 30 degrees, 25 degrees, 20 degrees, 15 degrees, 10 degrees, or 5 degrees away from perpendicular.

The term "connected" as it is used herein with reference to the second arm portion being "connected" to the lancet carrier is herein understood to mean that the second arm potion is in operative contact with the lancet carrier to draw the lancet carrier to a primed position when the first arm portion is moved toward the internal channel. During movement of the first arm portion toward the internal channel, the second arm portion may be directly in contact with the lancet carrier or it may be indirectly in contact with the lancet carrier, for example through a shuttle. In some cases the second arm portion may be in contact with the lancet carrier only when the first arm portion is moved toward the internal channel (e.g. upon priming the lancing device). In some other embodiments the second arm portion is always in contact with (i.e. attached to) the lancet carrier.

In a preferred embodiment, the first and second arm portions of the cantilevered priming arm are positioned relative to each other perpendicularly through a pivot point. The pivot point being the point the first and second arm portions intersect and preferably the point at which the cantilevered priming arm moves relative to the housing. In another embodiment the first and second arm portions of the cantilevered priming arm are positioned relative to each other up to 45 degrees away from perpendicular in either direction through the pivot point. For example 40 degrees, 35 degrees, 30 degrees, 25 degrees, 20 degrees, 15 degrees, 10 degrees, or 5 degrees away from perpendicular.

Figure 1B:
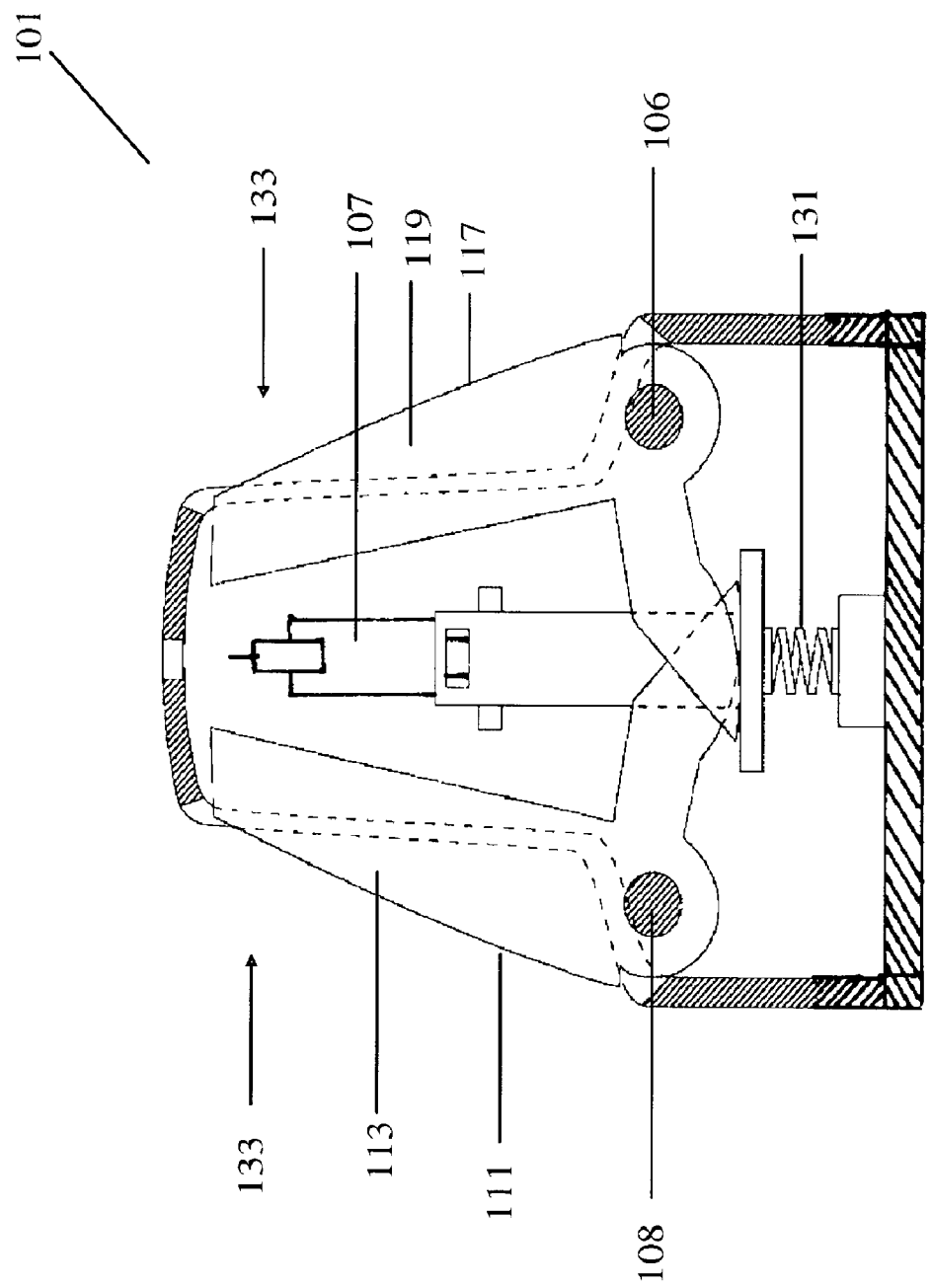
FIG. 1B is a cross-sectional top view of a lancing device in accordance with an embodiment of the present invention.
Figure 1C:
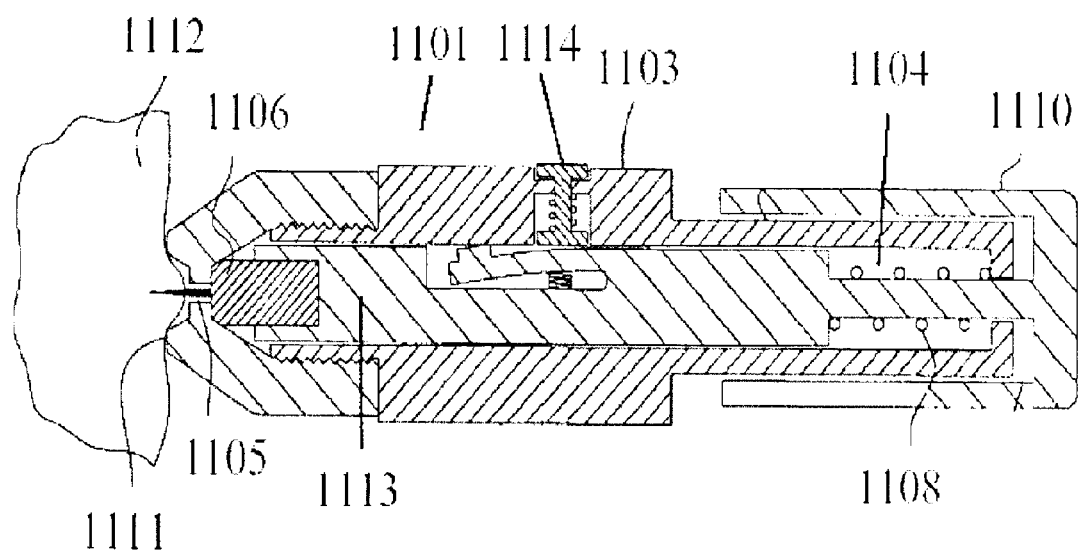
FIG. 1C is a cross-sectional side view of a prior art lancing device.

FIG. 1A shows a lancing device for lancing body tissue to result in a wound for bleeding in accordance with a preferred embodiment of the present invention. Lancing device 101 comprises:

(a) a housing 103 having an internal channel 105 extending within the housing 103 from a first lancing end 104 toward a second end of the housing 106;

(b) a lancet carrier 107 translationally mounted within the internal channel 105 for carrying a lancet 109 along a strike path of the lancet carrier 107, said strike path starting at a primed position toward the second end 106 of the housing 103 and extending to a lanced position at the first lancing end 104 of the housing 103, (c) a lancet driver in the form of a spring (shown in FIGS. 3A, 3B, 3C, 4A, 4B, and 4C) for storing energy and then driving the lancet carrier along the strike path from the primed position to the lanced position; and (d) a first cantilevered priming arm 111 comprising a first arm portion 113 that is generally parallel to the internal channel 105 and a second arm portion 115 that is generally perpendicular to the internal channel, wherein the second arm portion 115 is connected to the lancet carrier 107, (e) a second cantilevered priming arm 117 comprising a first arm portion 119 that is generally parallel to the internal channel 105 and a second arm portion 121 that is generally perpendicular to the internal channel 105, said first 111 and second 117 cantilevered priming arms being disposed on opposing sides of the internal channel 105, (f) a shuttle 123 disposed within the internal channel 105, wherein the shuttle 123 connects the first 111 and second 117 cantilevered priming arms to the lancet carrier 107, said shuttle 123 and lancet carrier 107 comprising a protrusion 125 and correspond depression 127 that engage to draw the lancet carrier 107 to a primed position and that release to fire the device 101 (In FIG. 1A protrusion 125 is disposed on the lancet carrier 107 while depression 127 is made in shuttle 123);

(g) a bump 129 (bumps 129 shown in FIG. 1A) disposed on either of the shuttle 123 or the housing 103 and a track (shown in FIGS. 3A, 3B, 3C, 4A, 4B, and 4C) disposed on the other of the shuttle 123 or the housing 103, said bump 129 and said track engage to tip the shuttle 123 as the lancet carrier 107 is drawn to the primed position, such that after the lancet carrier 107 reaches the primed position the protrusion 125 and corresponding depression 127 disengage thereby releasing energy stored in the lancet driver and firing the device 101, (h) a lancet carrier return spring (shown in FIGS. 4A, 4B, 4C) that interacts with the lancet carrier 107 to return the lancet carrier 107 to a resting position within the internal channel 105 after the device 101 is fired, (i) a shuttle return spring 131 compressed by the shuttle 123 when the lancet carrier 107 is drawn toward the primed position, said shuttle return spring 131 drives the cantilever arms 111, 117 to a resting position (as shown in FIG. 1A) and drives the shuttle 123 along the strike path toward the lancet carrier 107 located in a resting position to engage the protrusion 125 and corresponding depression 127 upon release of the cantilever priming arms 111, 117, and (j) a lancet 109 disposed within the lancet carrier 107, wherein movement of the first arm portions 113, 119 of the first 111, the second 117, or both the first 111 and the second 117 cantilever priming arms draws the lancet carrier 107 toward the primed position and stores energy in the lancet driver.

FIG. 1B shows the preferred lancing device described above with regard to FIG. 1A wherein the cantilever priming arms 111, 117 are moved toward the internal channel of the device around pivot points 106, 108. As the first portions 113, 119 of the first 111 and second 117 cantilever priming arms are moved 133 toward the internal channel 105, the lancet carrier 107 is drawn toward the primmed position. As lancet carrier 107 is drawn to the primed position, shuttle return spring 131 is compressed.

Figure 2A:
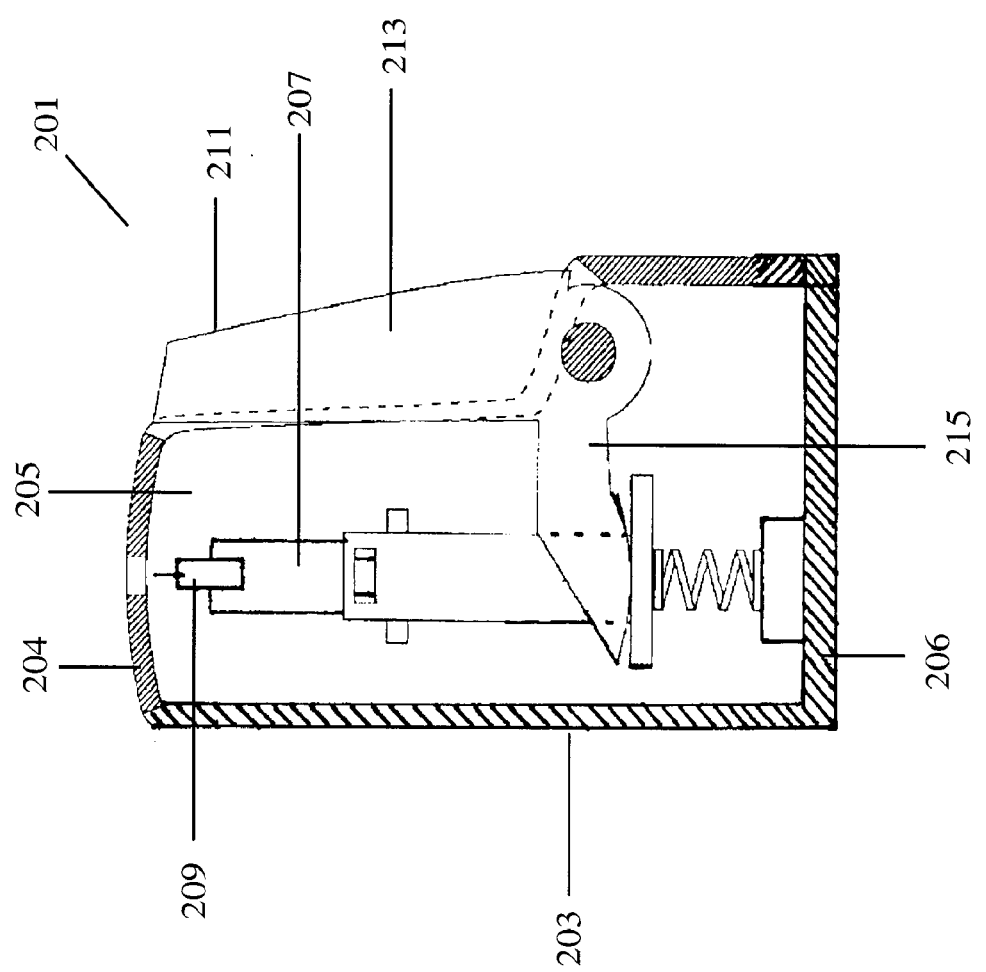
FIG. 2A is a cross-sectional top view of a lancing device in accordance with an embodiment of the present invention.
Figure 2B:
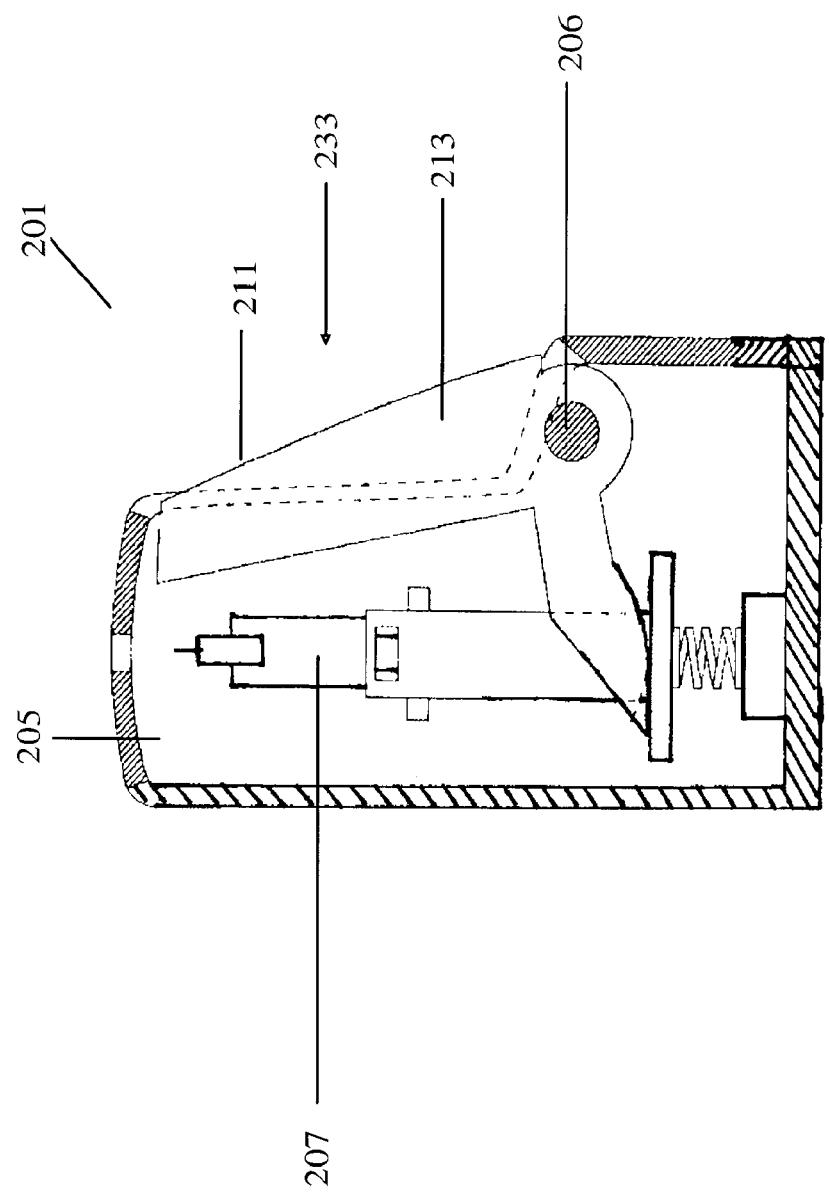
FIG. 2B is a cross-sectional top view of a lancing device in accordance with an embodiment of the present invention.

FIGS. 2A and 2B show cross-sectional top views of another embodiment of the present invention. In FIG. 2a a lancing device 201 is shown comprising:

(a) a housing 203 having an internal channel 205 extending within the housing 203 from a first lancing 204 end toward a second end 206 of the housing 203;

(b) a lancet carrier 207 translationally mounted within the internal channel 205 for carrying a lancet 209 along a strike path of the lancet carrier 207, said strike path starting at a primed position toward the second end 206 of the housing 203 and extending to a lanced position at the first lancing end 204 of the housing 203, (c) a lancet driver in the form of a spring (shown in FIGS. 3A, 3B, 3C, 4A, 4B, and 4C) for storing energy and then driving the lancet carrier 207 along the strike path from the primed position to the lanced position; and (d) a first cantilevered priming arm 211 comprising a first arm portion 213 that is generally parallel to the internal channel 205 and a second arm portion 215 that is generally perpendicular to the internal channel 205, wherein the second arm portion 215 is connected to the lancet carrier 207, wherein movement of the first arm portion 211 toward the internal channel 205 draws the lancet carrier 207 to a primed position and stores energy in the lancet driver.

FIG. 2B shows the lancing device described in FIG. 2A wherein the cantilever priming arm 211 is moved toward the internal channel of the device around pivot point 206. As the first portion 213 of the first cantilevered priming arm 211 is moved 233 toward the internal channel 205, the lancet carrier 207 is drawn toward the primed position.

Figure 3A:
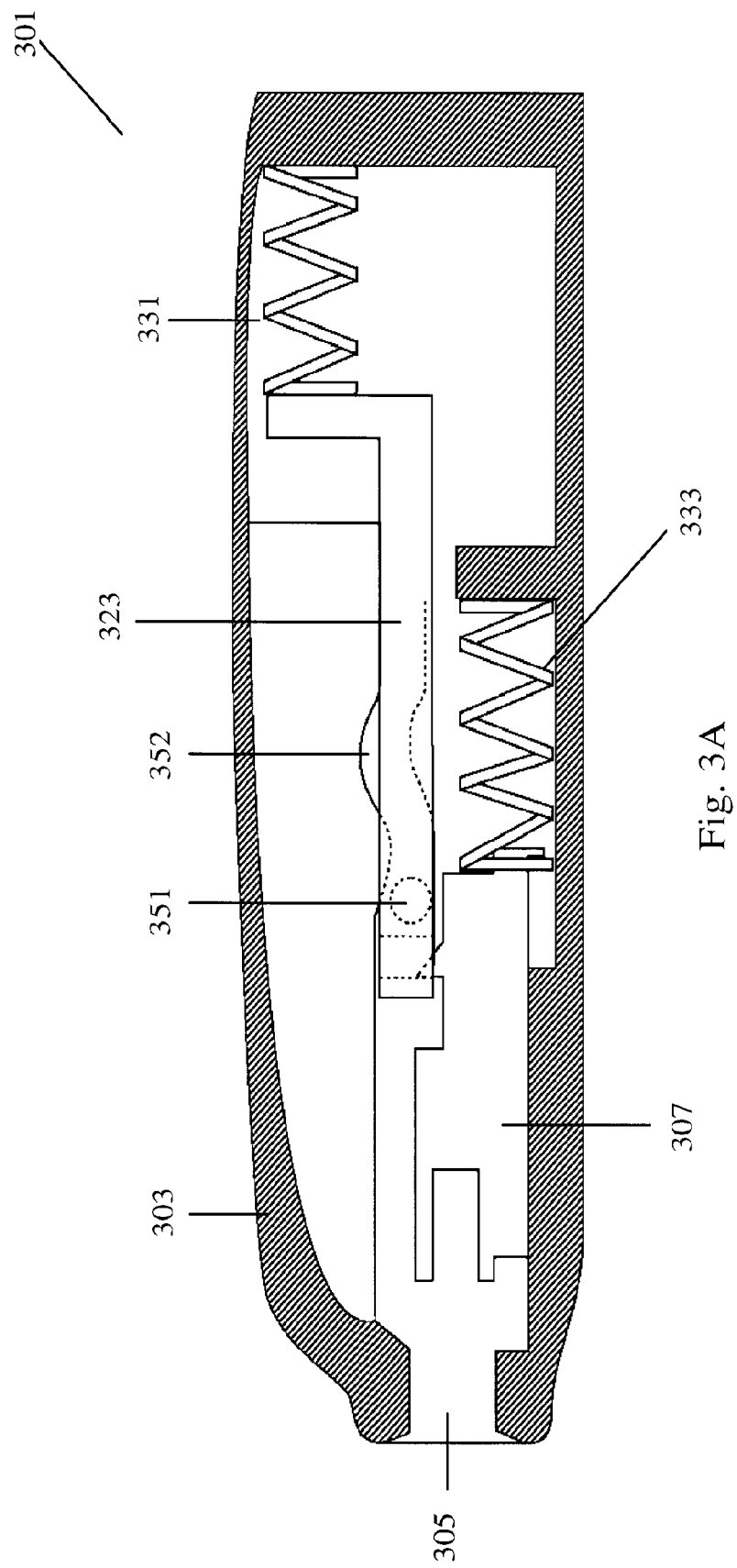
FIG. 3A is a cross-sectional side view of a lancing device in accordance with an embodiment of the present invention.
Figure 3B:
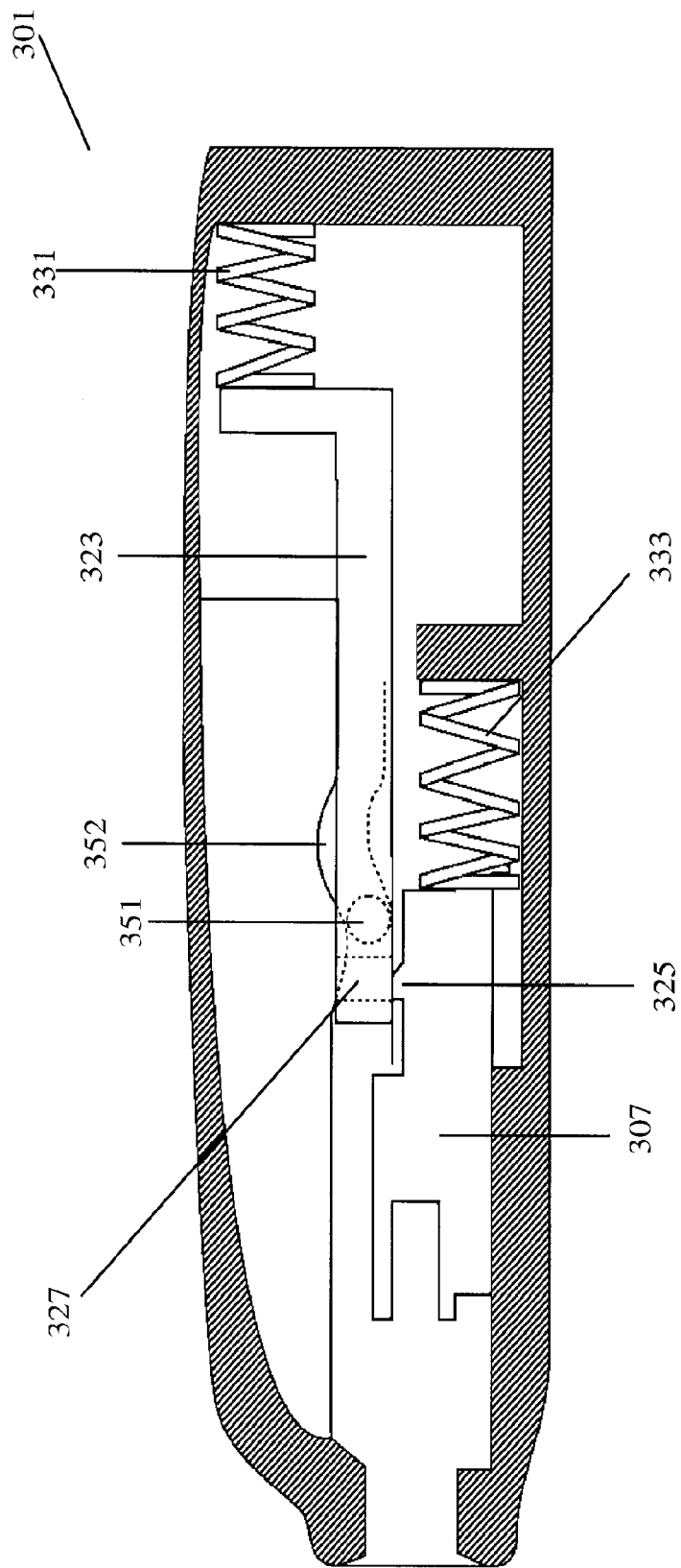
FIG. 3B is a cross-sectional side view of a lancing device in accordance with an embodiment of the present invention.
Figure 3C:
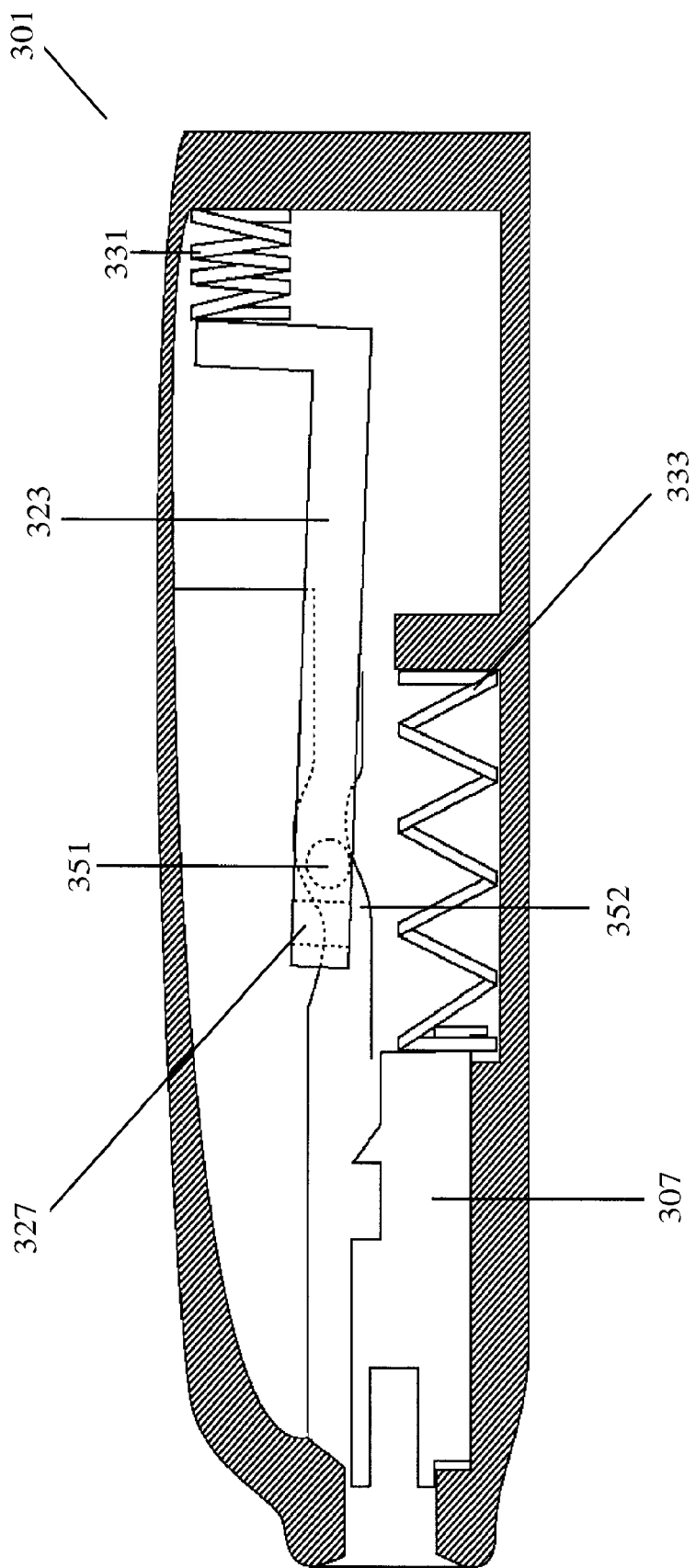
FIG. 3C is a cross-sectional side view of a lancing device in accordance with an embodiment of the present invention.

FIGS. 3A, 3B, and 3C show a cross-sectional side views of the inner workings at different stages of priming and firing of a preferred device of the present invention. In the present embodiment, the device is designed such that cocking and firing are accomplished in a single movement of the cantilevered priming arms. FIG. 3A depicts the lancet carrier 307 in a relaxed position. FIG. 3B shows the device 301 as the lancet carrier 307 is drawn toward a primed position. FIG. 3C shows the device 301 after it has been fired while the lancet carrier 307 is in a lancing position and prior to the release of the cantilevered priming arms.

FIG. 3A shows the device 301 while the lancet carrier is in resting position and prior to the release of the cantilevered priming arms. Device 301 has, inter alia, a housing 303, an internal channel 305, a lancet carrier 307, a shuttle 323, a shuttle return spring 331, and a lancet driver, spring 333. The device further comprises, a bump 351 disposed on either of the shuttle 323 or the housing 303 and a track 352 disposed on the other of the shuttle 323 or the housing 303. Here bump 351 is disposed on shuttle 323 and track 352 is disposed in interacting alignment in housing 303.

As depicted in FIGS. 3B and 3C, bump 351 and the track 352 engage to tip the shuttle 323 as the lancet carrier 307 is drawn to the primed position. As the lancet carrier 307 is drawn toward a primed position, bump 351 which is disposed on shuttle 323 rides along track 352. Track 352 is formed in the housing such that bump 351 is lifted as the lancet carrier draws near a primed position thereby lifting the shuttle 323. As the shuttle 323 is lifted and after the lancet carrier 307 reaches the primed position the protrusion 325 and corresponding depression 327 disengage thereby releasing energy stored in the lancet driver, spring 333 and firing the device 301.

Protrusion 325 and depression 327 are designed such that they interact to draw the lancet carrier 307 toward a primed position, disengage to fire the device 301, and re-engage upon release of the cantilevered priming arms for subsequent priming and firing of the device 301. The protrusion 325 may be formed on either of the lancet carrier 307 or the shuttle 323, and the corresponding depression 327 may be formed on the other of the lancet carrier 307 or shuttle 323. Preferably, and as depicted in FIG. 3A, 3B, and 3C, the protrusion 325 is disposed on the lancet carrier 307 and is triangularly shaped having a flat priming surface. The depression 327 also has a flat priming surface to engage flat priming surface of the protrusion 325 in priming alignment. As priming force is applied by the shuttle 323 to the lancet carrier 307, the flat priming surface of the protrusion 325 engages a flat priming surface of the depression 327 such that the lancet carrier 307 is drawn to a primed position without prematurely disengaging and prematurely firing the device 301. In a preferred embodiment, while the lancet carrier 307 and shuttle 323 are in priming alignment, the flat priming surface of the protrusion 325 and the flat priming surface of the depression 327 will interact such that the plane of priming interaction will be perpendicular to the direction of the strike path.

After device 301 has been fired, the lancet driver, spring 333 also serves to return the lancet carrier 307 toward its resting position. When a user releases the cantilevered priming arms the shuttle return spring 331 (which is compressed by the shuttle 323 when the lancet carrier 307 is drawn to a primed position) drives the cantilevered priming arms toward their resting position and drives the shuttle 323 along the strike path toward the lancet carrier 307, located in its resting position, to engage the protrusion 325 and corresponding depression 327 upon release of the cantilever priming arms. Protrusion 325 is further shaped such that as the shuttle 323 returns toward the lancet carrier 307, the shuttle 323 may ride up along a second slanted flat surface of the triangularly shaped protrusion 323 and fall into priming alignment as described above.

Figure 4A:
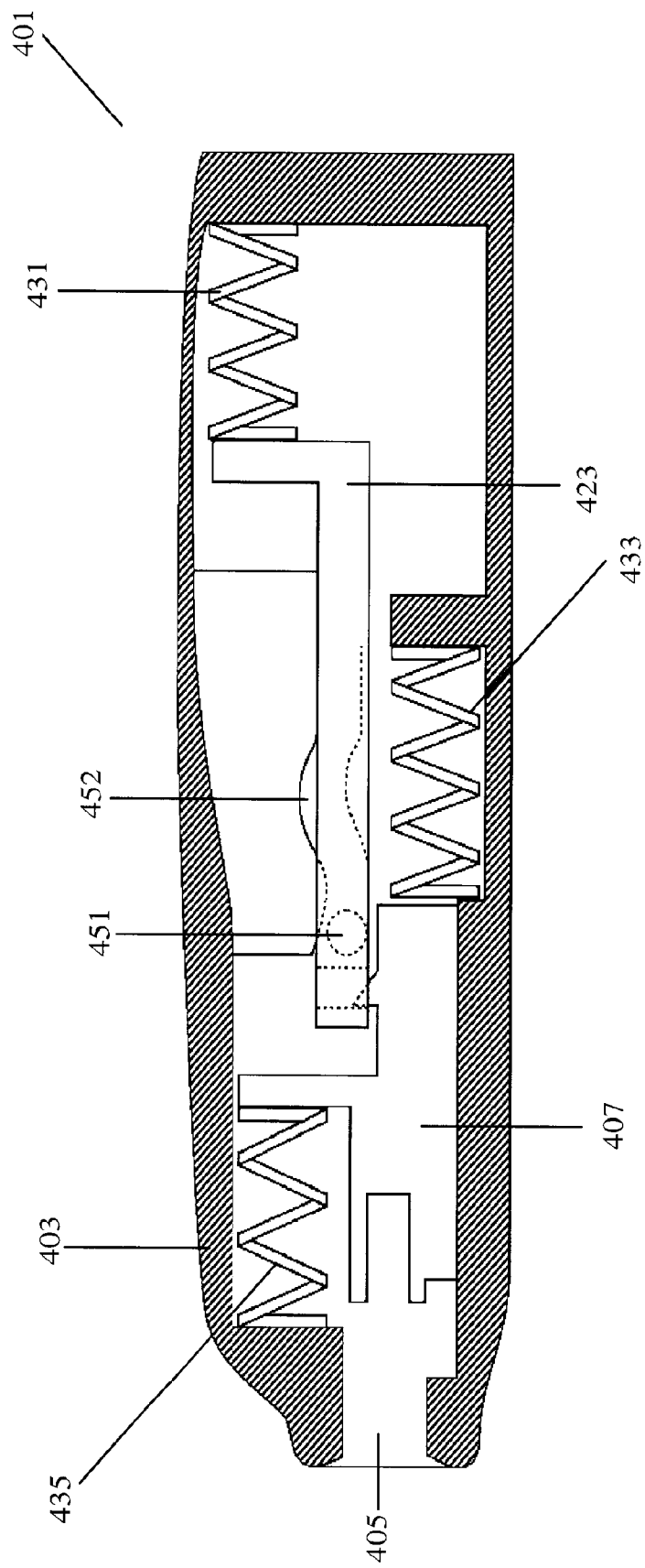
FIG. 4A is a cross-sectional side view of a lancing device in accordance with an embodiment of the present invention.
Figure 4B:
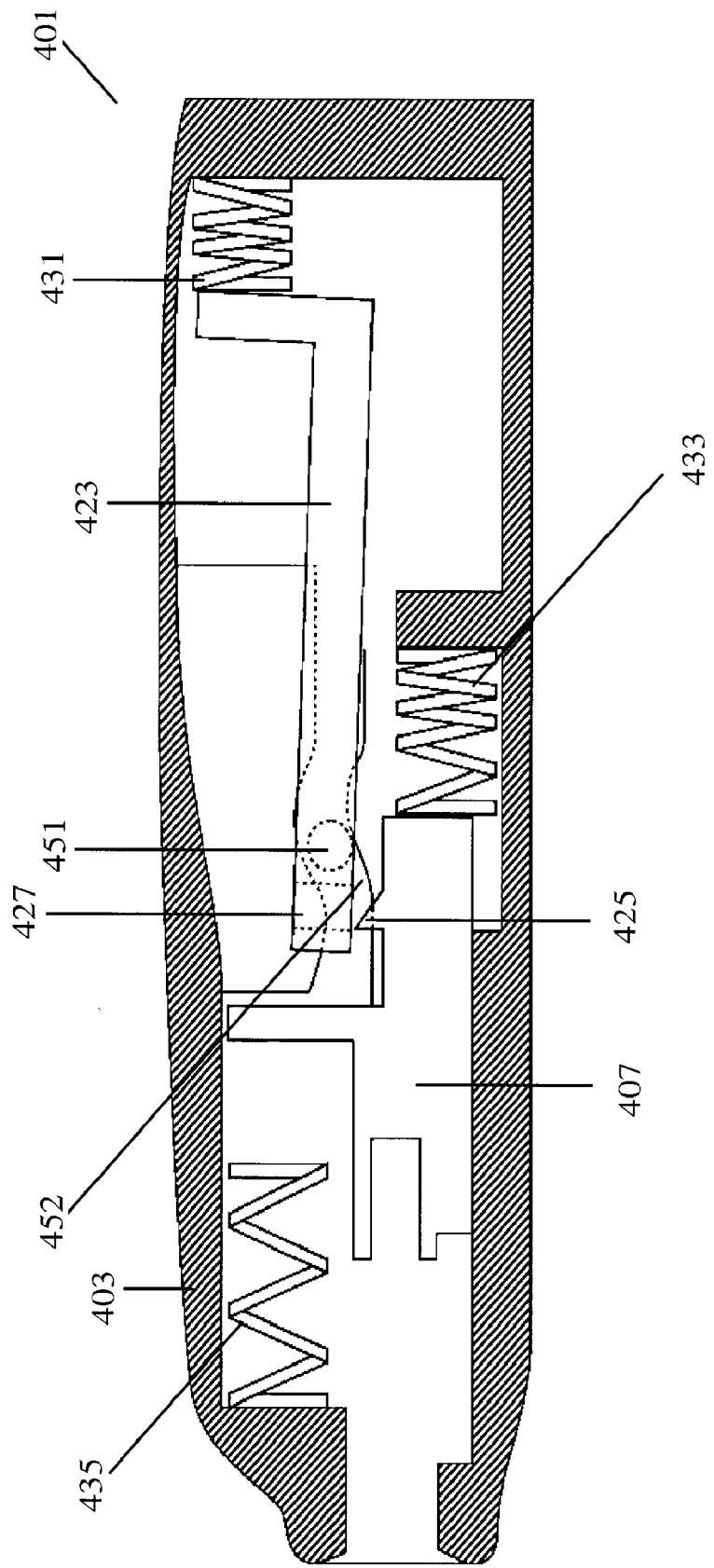
FIG. 4B is a cross-sectional side view of a lancing device in accordance with an embodiment of the present invention.
Figure 4C:
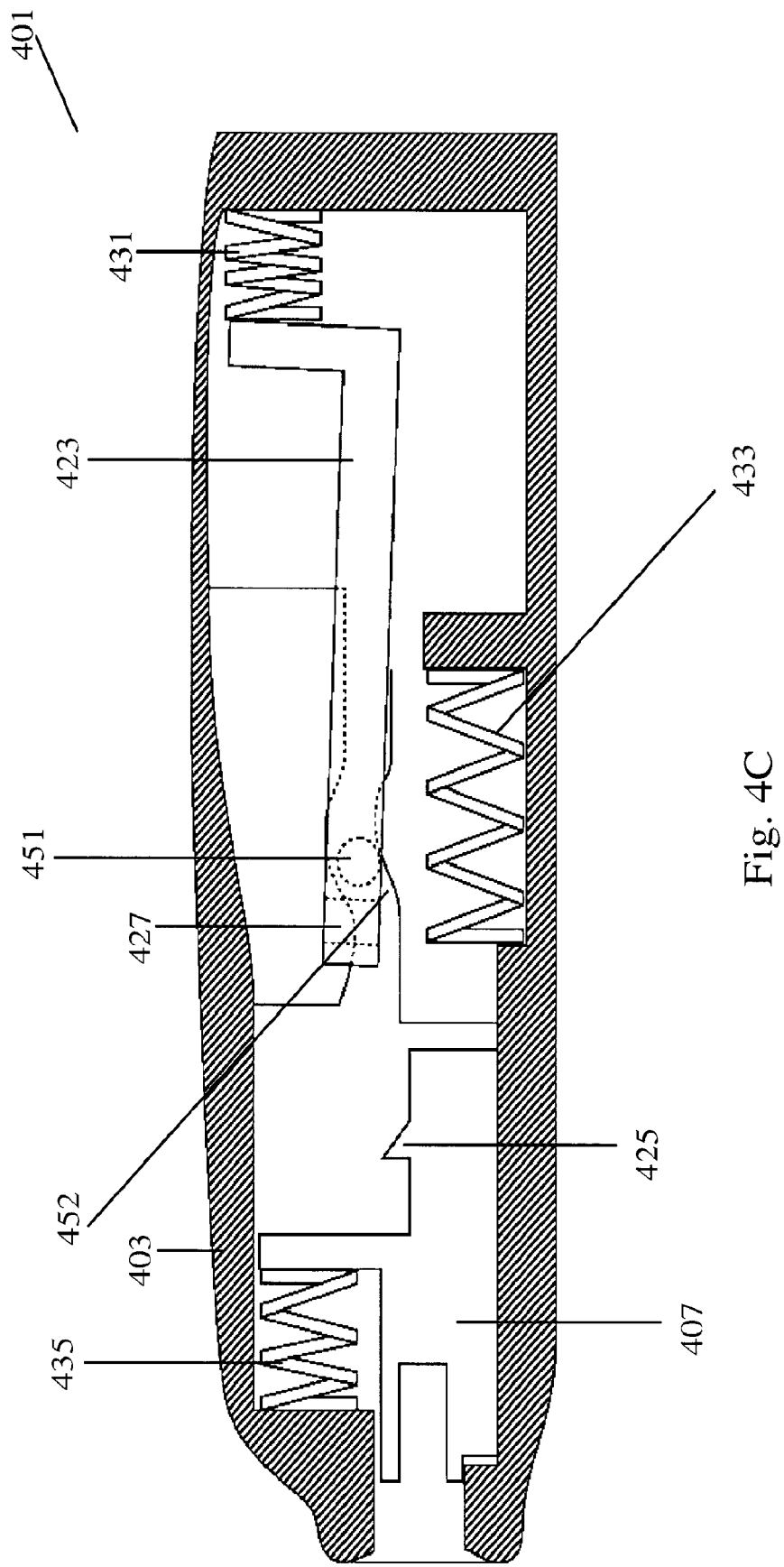
FIG. 4C is a cross-sectional side view of a lancing device in accordance with an embodiment of the present invention.

FIGS. 4A, 4B, and 4C show a cross-sectional side views of the inner workings at different stages of priming and firing of another preferred device of the present invention. In the present embodiment, the device is designed such that cocking and firing are accomplished in a single movement of the cantilevered priming arms. FIG. 4A depicts the lancet carrier 407 in a relaxed position. FIG. 4B shows the device 401 as the lancet carrier 407 is drawn toward a primed position. FIG. 4C shows the device 401 after it has been fired while the lancet carrier 407 is in a lancing position and prior to the release of the cantilevered priming arms.

FIG. 4A shows the device 401 while the lancet carrier is in resting position and prior to the release of the cantilevered priming arms. Device 401 has, inter alia, a housing 403, an internal channel 405, a lancet carrier 407, a shuttle 423, a shuttle return spring 431, a lancet driver, spring 433, and a lancet return spring 435. The device further comprises, a bump 451 disposed on either of the shuttle 423 or the housing 403 and a track 452 disposed on the other of the shuttle 423 or the housing 403. Here bump 451 is disposed on shuttle 423 and track 452 is disposed in interacting alignment in housing 403.

As depicted in FIGS. 4B and 4C, bump 451 and the track 452 engage to tip the shuttle 423 as the lancet carrier 407 is drawn to the primed position. As the lancet carrier 407 is drawn toward the primed position, bump 451 which is disposed on shuttle 423 rides along track 452. Track 452 is formed in the housing such that bump 451 is lifted as the lancet carrier draws near a primed position thereby lifting the shuttle 423. As the shuttle 423 is lifted and after the lancet carrier 407 reaches the primed position the protrusion 425 and corresponding depression 427 disengage thereby releasing energy stored in the lancet driver, spring 433 and firing the device 401.

Protrusion 425 and depression 427 are designed such that they interact to draw the lancet carrier 407 toward a primed position, disengage to fire the device 401, and re-engage upon release of the cantilevered priming arms for subsequent priming and firing of the device 401. The protrusion 425 may be formed on either of the lancet carrier 407 or the shuttle 423, and the corresponding depression 427 may be formed on the other of the lancet carrier 407 or shuttle 423. Preferably, and as depicted in FIG. 4A, 4B, and 4C, the protrusion 425 is disposed on the lancet carrier 407 and is triangularly shaped having a flat priming surface. The depression 427 also has a flat priming surface to engage flat priming surface of the protrusion 425 in priming alignment. As priming force is applied by the shuttle 423 to the lancet carrier 407, the flat priming surface of the protrusion 425 engages a flat priming surface of the depression 427 such that the lancet carrier 407 is drawn to a primed position without prematurely disengaging and prematurely firing the device 401. In a preferred embodiment, while the lancet carrier 407 and shuttle 423 are in priming alignment, the flat priming surface of the protrusion 425 and the flat priming surface of the depression 427 will interact such that the plane of priming interaction will be perpendicular to the direction of the strike path.

After device 401 has been fired, the lancet return spring 435 serves to return the lancet carrier 407 toward its resting position. When a user releases the cantilevered priming arms the shuttle return spring 431 (which is compressed by the shuttle 423 when the lancet carrier 407 is drawn to a primed position) drives the cantilevered priming arms toward their resting position and drives the shuttle 423 along the strike path toward the lancet carrier 407, located in its resting position, to engage the protrusion 425 and corresponding depression 427 upon release of the cantilever priming arms. Protrusion 425 is further shaped such that as the shuttle 423 returns toward the lancet carrier 407, the shuttle 423 may ride up along a second slanted flat surface of the triangularly shaped protrusion 423 and fall into priming alignment as described above.

In another embodiment, the lancing device of the present invention, may be designed such that priming and firing of the device occurs in two stages. For example, a user may prime the device by moving the cantilevered priming arm toward the internal channel of the device where the lancet carrier is placed into a locked and primed position and where energy is stored in the lancet driver. In a second step, a user may press a release button that releases the energy stored in the driver spring as the lancet carrier is driven along the strike path toward the skin the lancing end of the device.

In the figures discussed above, the lancet driver is shown as a coiled spring, which stores energy by being compressed. The invention, however is not limited to the use of coiled springs and other structures capable of storing energy upon displacement by the action of the cantilevered priming arm are within the scope of the invention. By way of non-limiting example, the lancet driver may be a leaf spring, an elastic band that is stretched or an elastomeric block that is compressed.

Figure 6:
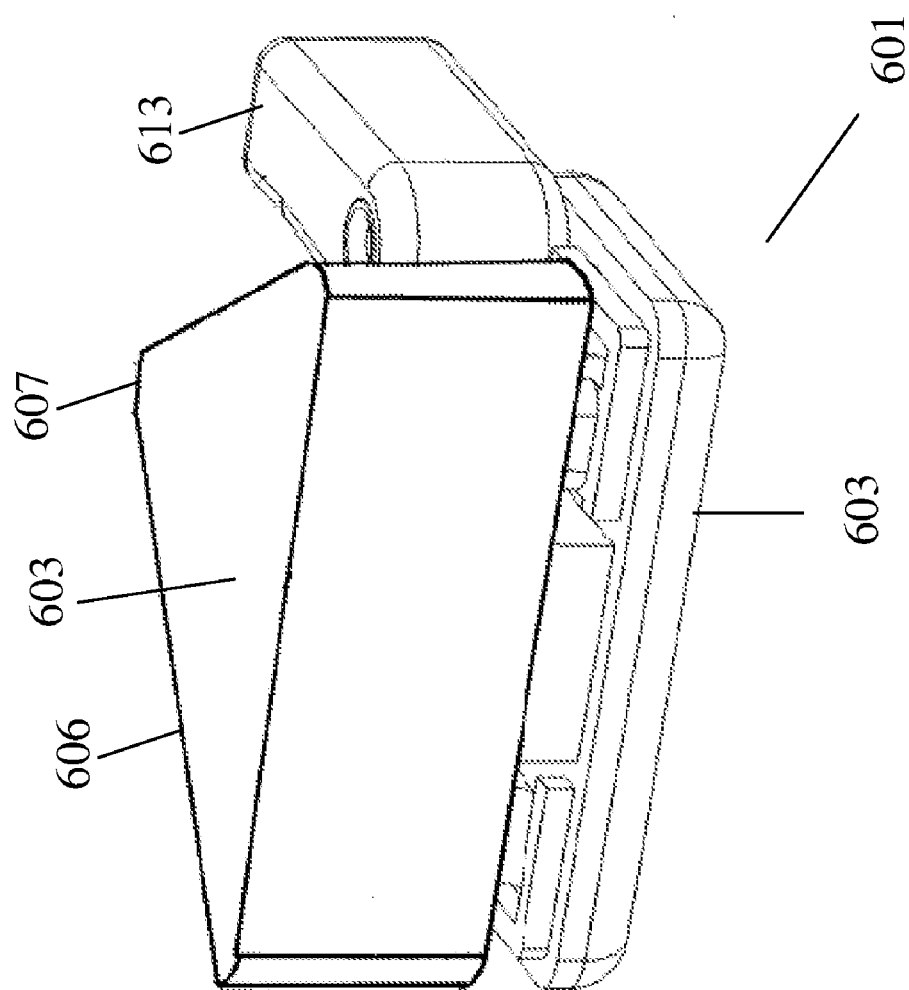
FIG. 6 is an isometric view of a lancing device in accordance with an embodiment of the present invention.

FIGS. 6, 7A, 7B, 7C, 7D, 7E, 7F, 7G, and 7H illustrate another preferred lancing device in accordance with the present invention. FIG. 6 illustrates an exploded view of a lancing device 601 having a first cantilevered priming arm 613 and housing 603. The lancing device has an internal channel disposed within the housing 603 extending from a lancing end 604 to a second end 606 of the housing 603. FIGS. 7A, 7B, 7C, 7D, 7E, 7F, 7G, and 7H illustrate the inner working of lancing device 601 (i.e. without housing top 603). For example lancing device 601, 701 in FIGS. 6, 7A, 7B, 7C, 7D, 7E, 7F, 7G, and 7H is for use with a lancet 709 for lancing body tissue to result in a wound for bleeding. Lancing device 701 comprises:

(a) a housing 603, 703 (housing top 603 shown in FIG. 6) having an internal channel extending within the housing 603, 703 from a first lancing end 604 toward a second end 606 of the housing 603, 703;

(b) a lancet carrier 707 translationally mounted within the internal channel for carrying a lancet 709 along a strike path 750 of the lancet carrier 707, said strike path 750 starting at a primed position toward the second end 606 of the housing and extending to a lanced position at the first lancing end of the housing 604, (c) a lancet driver (not shown in FIGS. 6, 7A, 7B, 7C, 7D, 7E, 7F, 7G, and 7H) for storing energy and then driving the lancet carrier 707 along the strike path 750 from the primed position to the lanced position; and (d) a first cantilevered priming arm 711 comprising a first arm portion 713 that is generally parallel to the internal channel and a second arm portion 715 that is generally perpendicular to the internal channel, wherein the second arm portion 715 is connected to the lancet carrier 707, wherein movement of the first arm portion 713 toward the internal channel draws the lancet carrier 707 to a primed position and stores energy in the lancet driver.

Figure 7A:
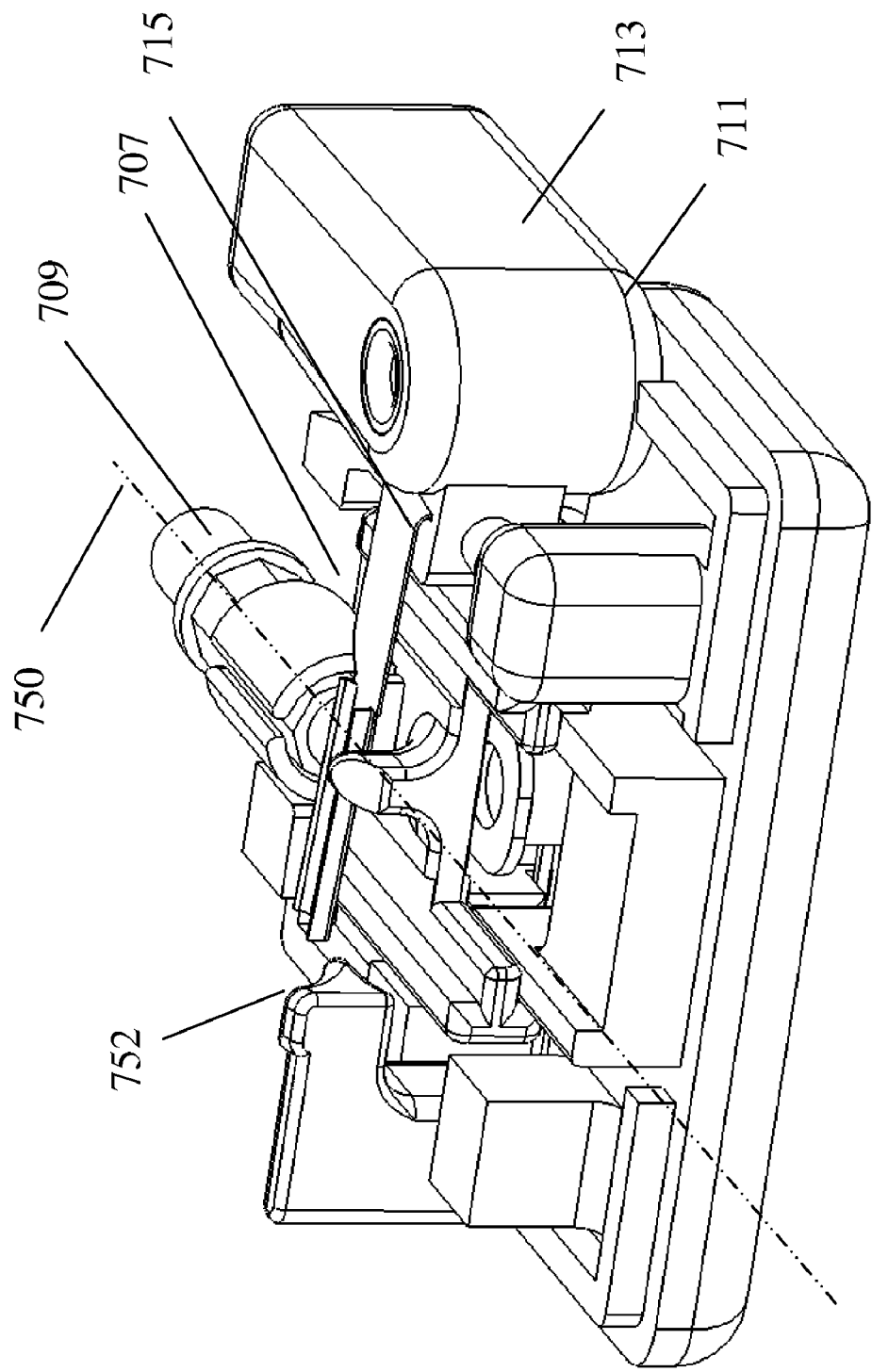
FIGS. 7A to 7H are a collection of isometric and top views showing the operation a lancing device in accordance with a preferred embodiment of the present invention.
Figure 7B:
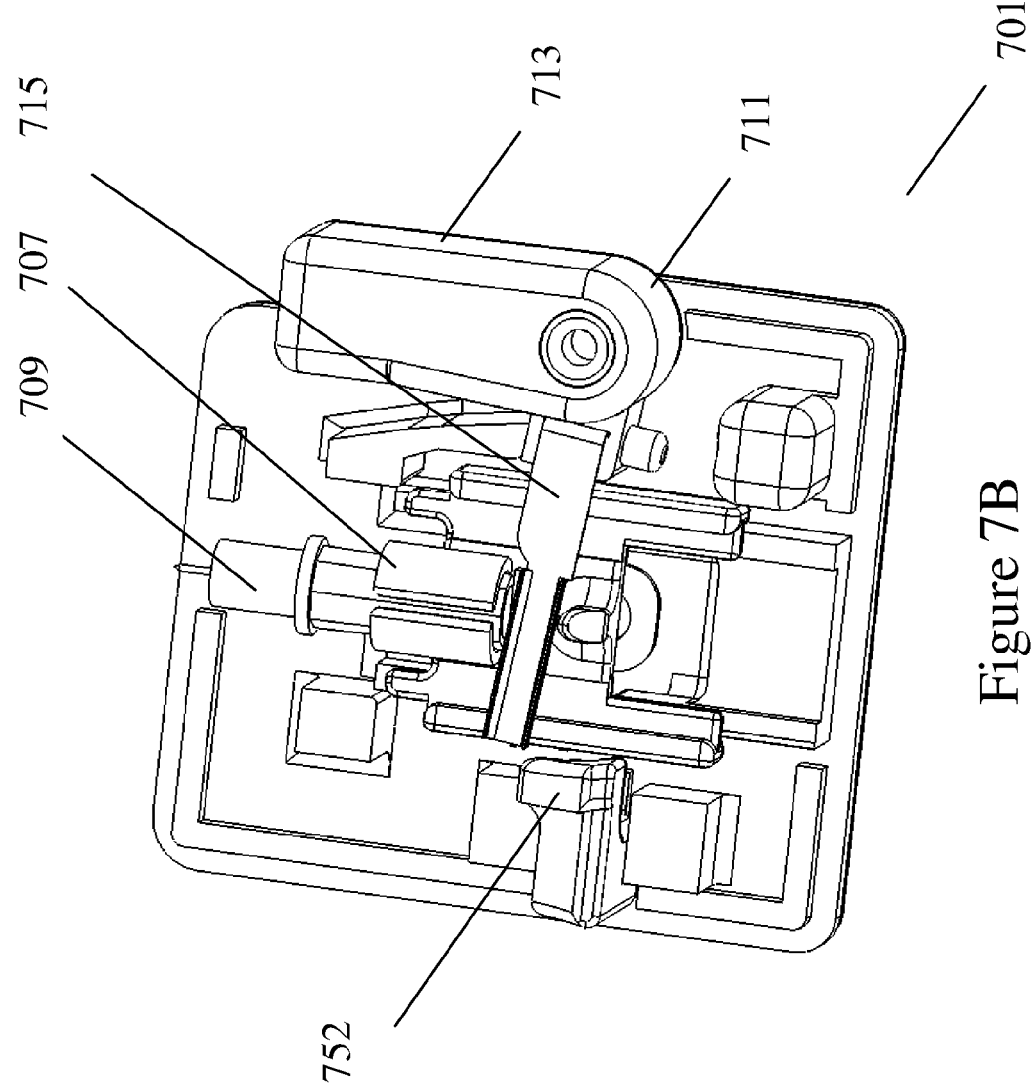
Figure 7C:
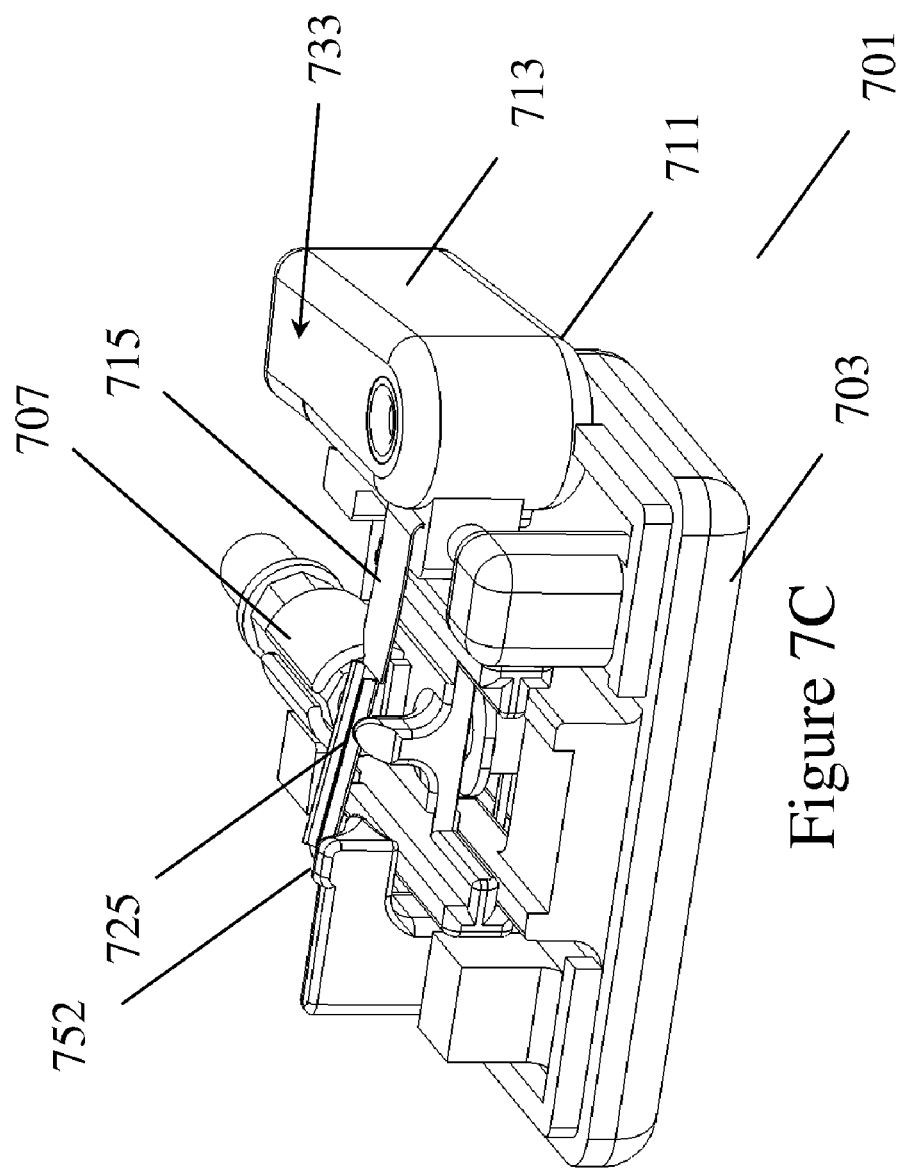
Figure 7D:
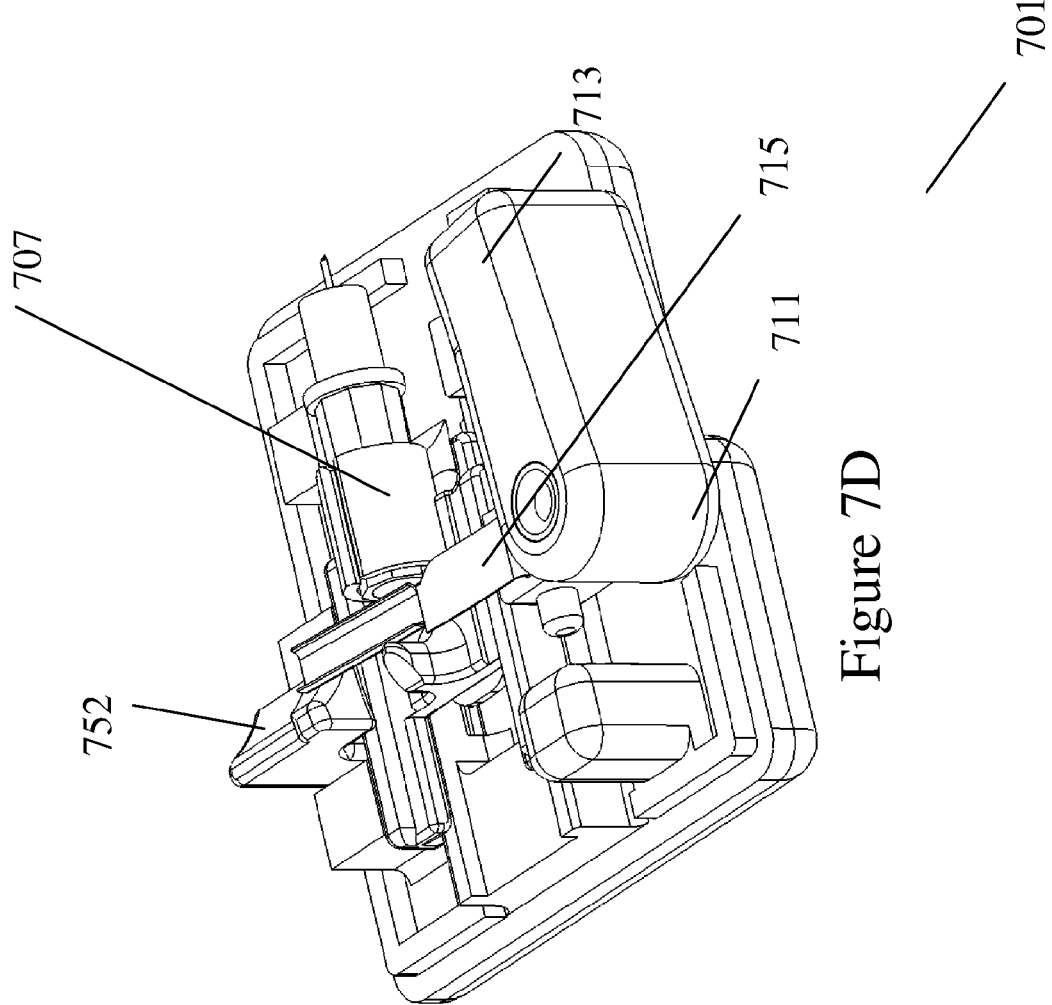
Figure 7E:
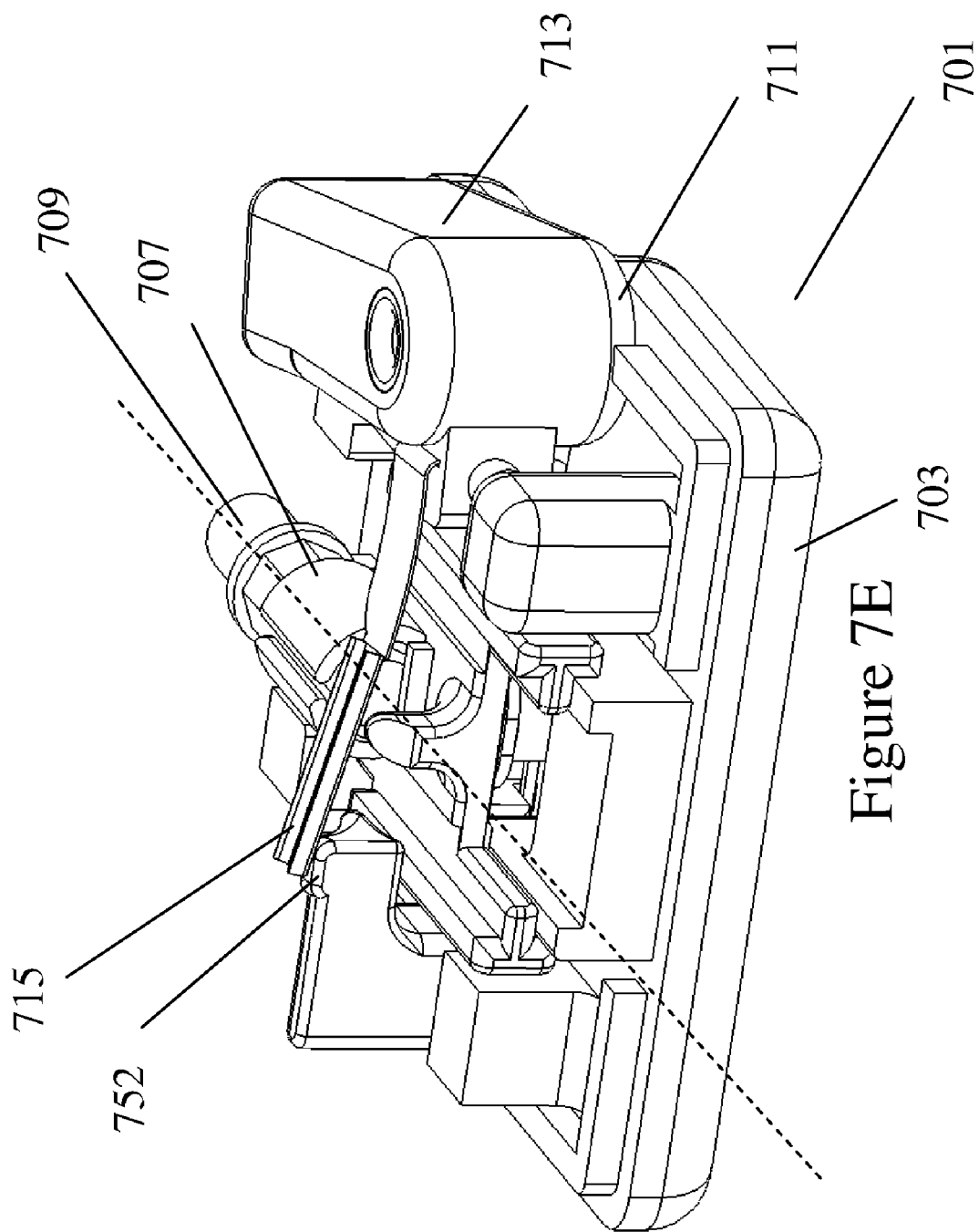
Figure 7F:
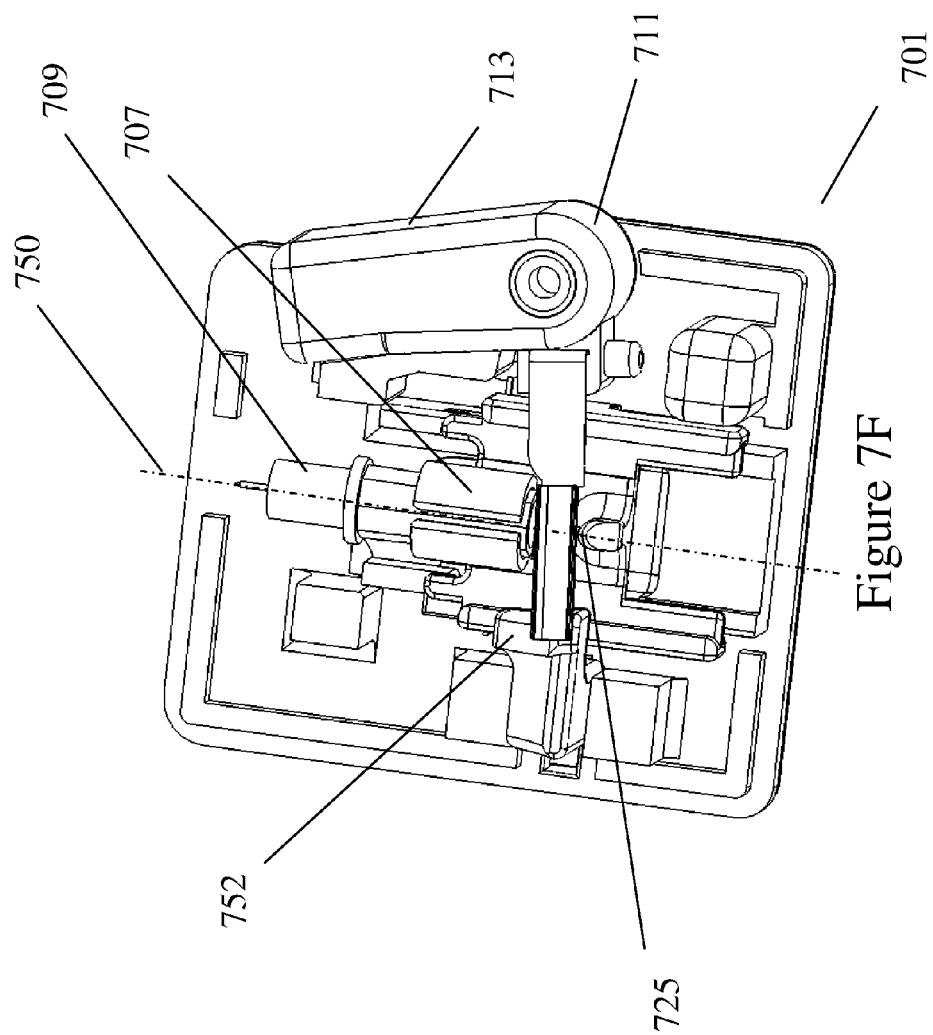

FIGS. 7A, 7B, 7C, 7D, 7E, 7F, 7G, and 7H show the lancing device 701 at different stages of operation. FIG. 7A is an isometric view and FIG. 7B is a top view lancing device 701 in a resting position. Here second arm portion 715 of the first cantilevered priming arm 711 is connected to (e.g. in operative contact with) with lancet carrier 707 at the priming protrusion 725 of the lancet carrier 707. Lancing device 701 also has a moveable firing ramp 752 that can be set by the user in either a safety position (as it is depicted in FIG. 7A and 7B) or a fire position as depicted in FIGS. 7C, 7D, 7E, 7F, 7G, and 7H. When the firing ramp 752 is in a safety position the device will not fire regardless of movement of the first arm portion 713 of the priming arm 711. As depicted in FIGS. 7C (an isometric view) and 7D (a top view) when the first arm portion 713 of the priming arm 711 is moved 733 toward the internal channel of the lancing device 701 energy is stored in the lancet driver (not shown) as the lancet carrier is drawn toward a primed position via the interaction of the second arm portion 715 and the priming protrusion 725 of the lancet carrier 707. As depicted in FIGS. 7C, 7D, 7E, 7F, 7G, and 7H the firing ramp 752 has been placed in the fire position. As the first arm portion 713 is moved further toward the internal channel the lancet carrier 707 is drawn closer to the primed position and the second arm portion 715 interacts with firing ramp 752. As depicted in FIGS. 7E (isometric view) and 7F (top view) of the lancing device 701, when placed in the fire position the firing ramp 752 serves to lift the second arm portion 715 and disengage the connection of the second arm portion 715 from the priming protrusion 725 of the lancet carrier 707 when the lancet carrier 707 reaches a primed position. Once the second arm portion 715 is disengaged from the lancet carrier 707, the lancing device 701 fires and energy stored in the lancet driver (not shown) is released thereby propelling the lancet carrier 707 and lancet 709 along the strike path to the lanced position depicted in FIGS. 7G (isometric view) and 7H (top view). At the lanced position a tissue penetration portion 760 of lancet 709 extend past the housing 703 for lancing interaction with a user's skin.

Figure 7G:
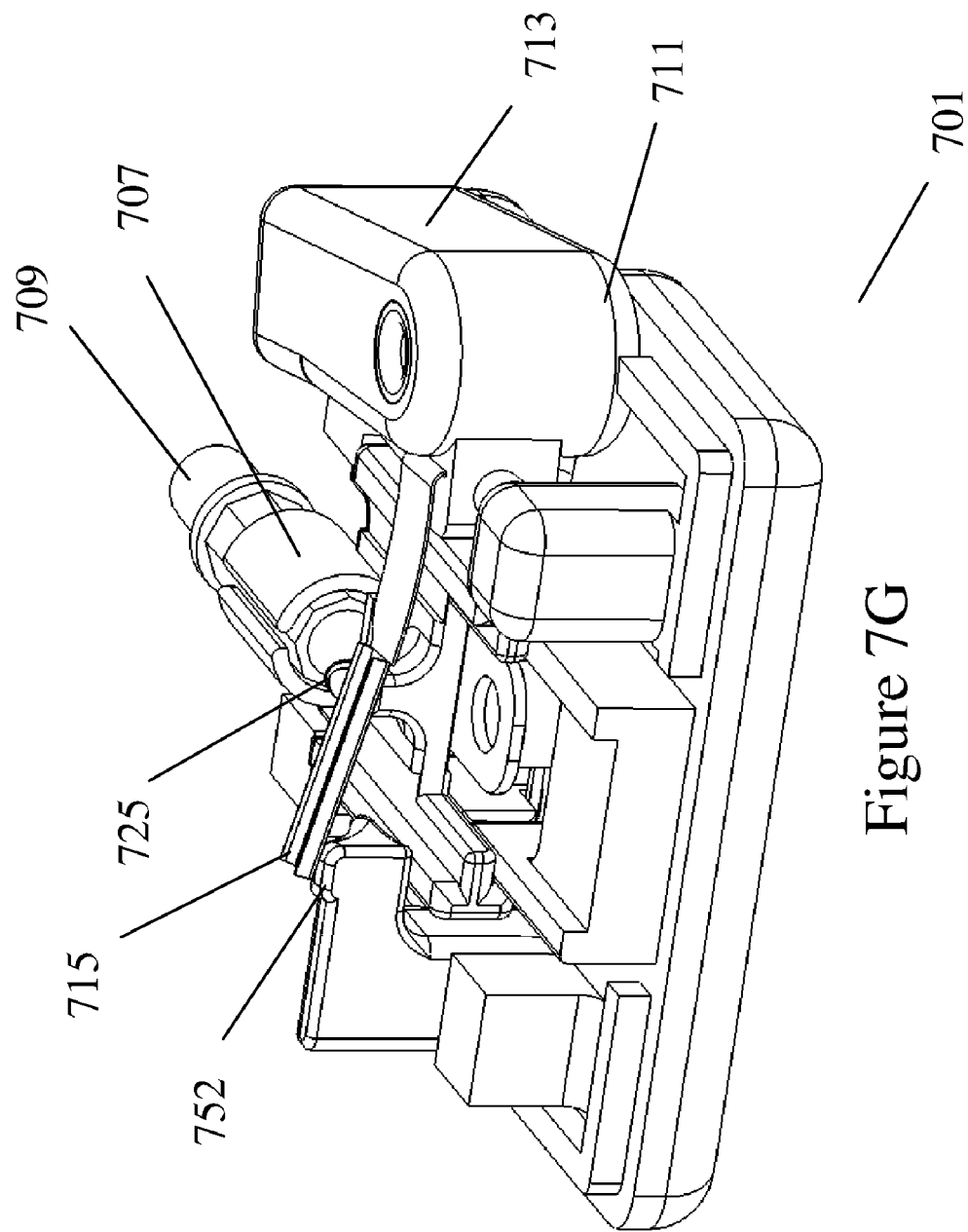
Figure 7H:
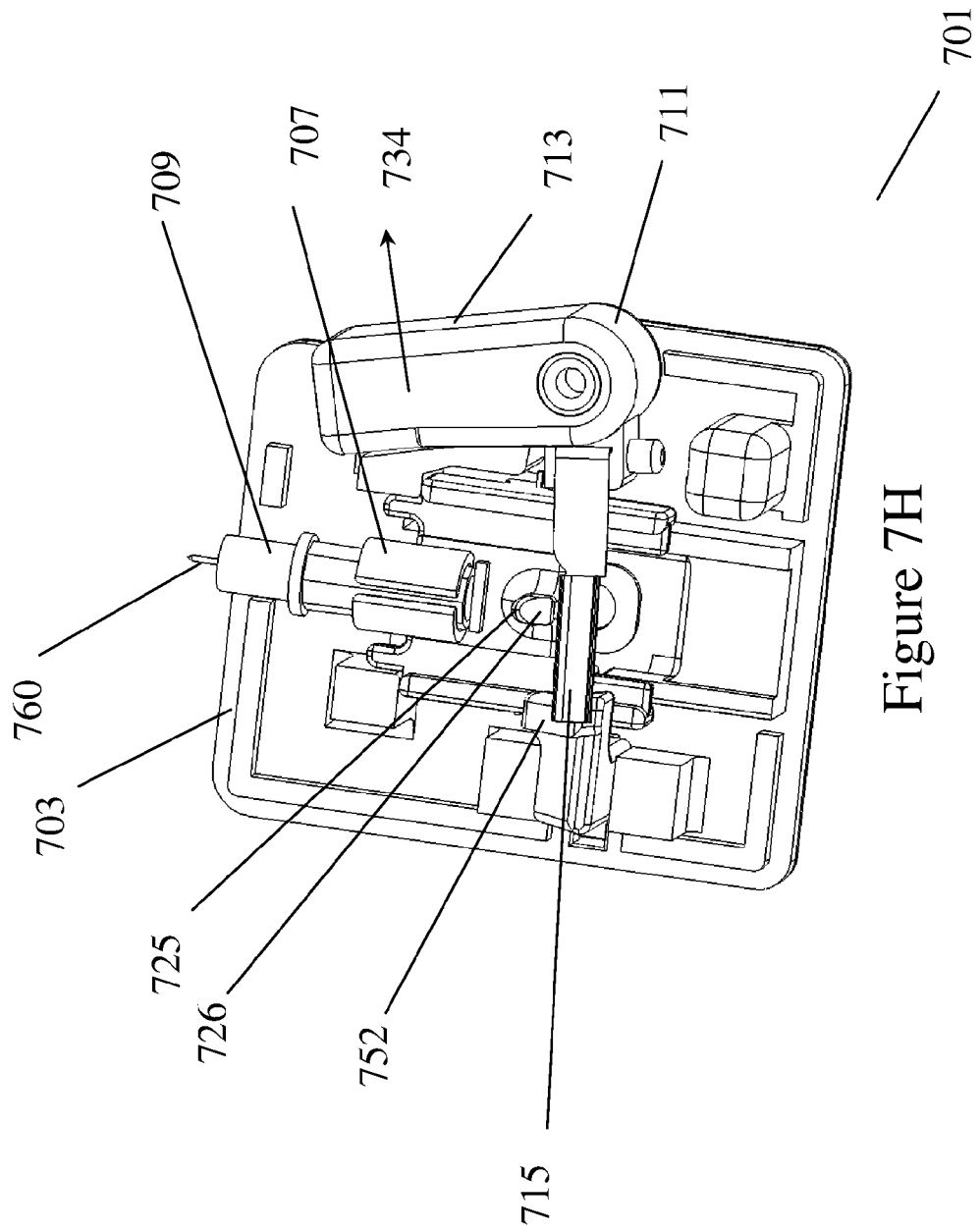
Figure 8:
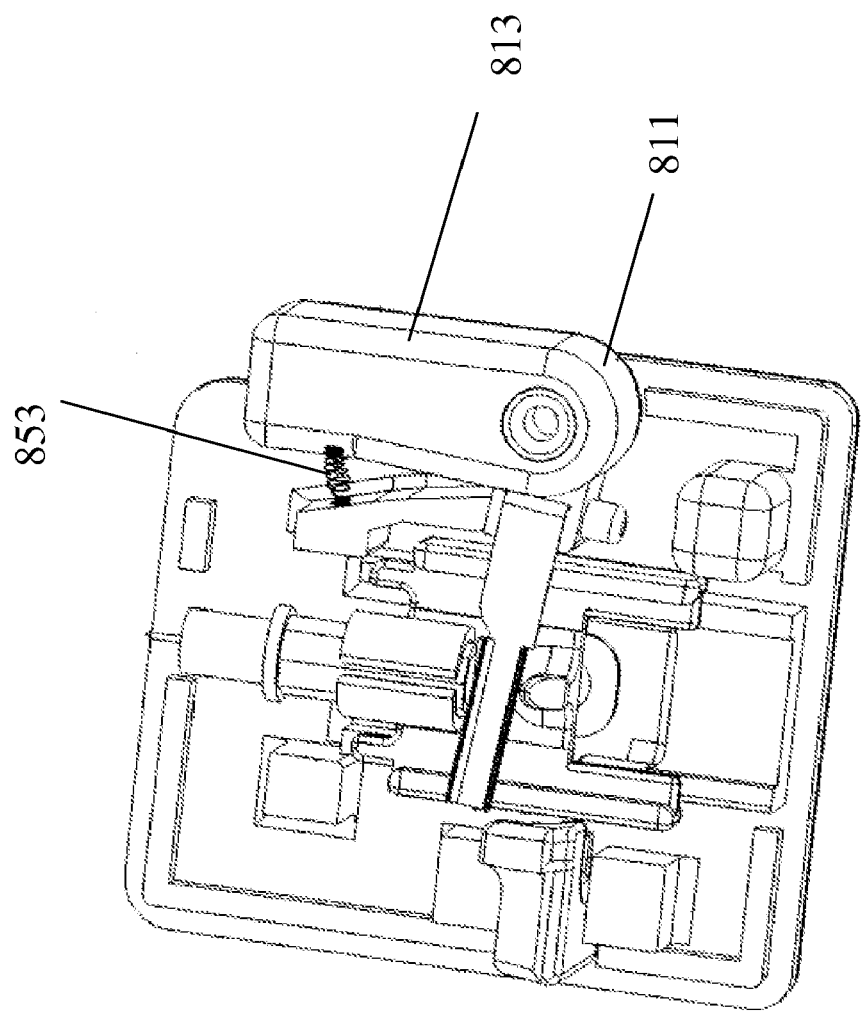
FIG. 8 is a top view of a lancing device in accordance with an embodiment of the present invention.

After the lancing device 701 has fired the device 701 may be reused. In order to maintain sanitary lancing procedure it is preferred that the used lancet 709 is disposed of and a new lancet is used in each subsequent lancing. To reset the device from a lanced position as depicted in FIGS. 7G and 7H the priming ramp 752 is moved to the safety position and the first arm portion 713 is moved 734 away from the internal channel whereby the second arm portion 715 is drawn toward priming protrusion 725. Second arm portion interacts with a slanted side 726 of priming protrusion 725 where the second arm portion 715 is lifted over the priming protrusion 725 and settles back into the resting position as depicted in FIGS. 7A and 7B. The lancing device 701 is then ready to be used again. In a preferred embodiment shown in FIG. 8, first arm portion 813 has a return spring 853 associated with it where after a user releases the first arm portion 813 after lancing, the return spring 853 biases the first arm portion 813 toward the resting position, thereby returning the device 801 to the resting position after its use. In another embodiment, the lancing devices depicted in any of FIGS. 6 through 8 would further comprises a second cantilevered priming arm disposed on the opposing side of the internal channel. This second cantilevered arm would have mirrored operation (about the internal channel and the strike path) to the first cantilevered arm and would have similar interaction with the lancet carrier and a second firing ramp also disposed within the internal channel. In this latter embodiment, movement of the first arm portions of either or both of the cantilevered arms toward the internal channel would draw the lancet carrier toward a primed position.

In a further embodiment a lancet and an analyte monitoring meter are combined in a single device having a cantilevered priming arm described herein. The combination allows for the reduction of the number of pieces of equipment required to perform an analyte measurement. For example U.S. Pat. Nos. 4,627,445, 6,192,891, and 6,840,912, all of which are herein incorporated by reference, disclose the combination of a analyte meter with a lancet in a single device. In the present embodiment the lancet housing described above provides mounting locations for a lancet assembly having the cantilevered priming arm as well an analyte monitoring meter. The analyte monitoring meter may be formed integral with the lancet within the lancet housing or it may be detachable from the lancet housing to form a combined device. The combined device will have lancet features as described above and will include a housing, a display, a test strip interface, and a processor programmed to calculate and store the concentration of an analyte, preferably glucose, in a blood sample applied to a test strip. The housing has an opening for receiving the meter display as well as an opening for receiving a diagnostic test strip inserted into the test strip interface of the analyte monitoring meter. The display opening and test strip opening of the housing may be located anywhere along the housing, however, it is preferred that the display opening be on the side of the annular housing while the test strip opening be located at the lancing end of the housing. The analyte monitoring meter of the present invention is not limited. However, the analyte monitoring meter described in U.S. patent publication No. US 2005/0265094, herein incorporated by reference, is particularly preferred.

Figure 5A:
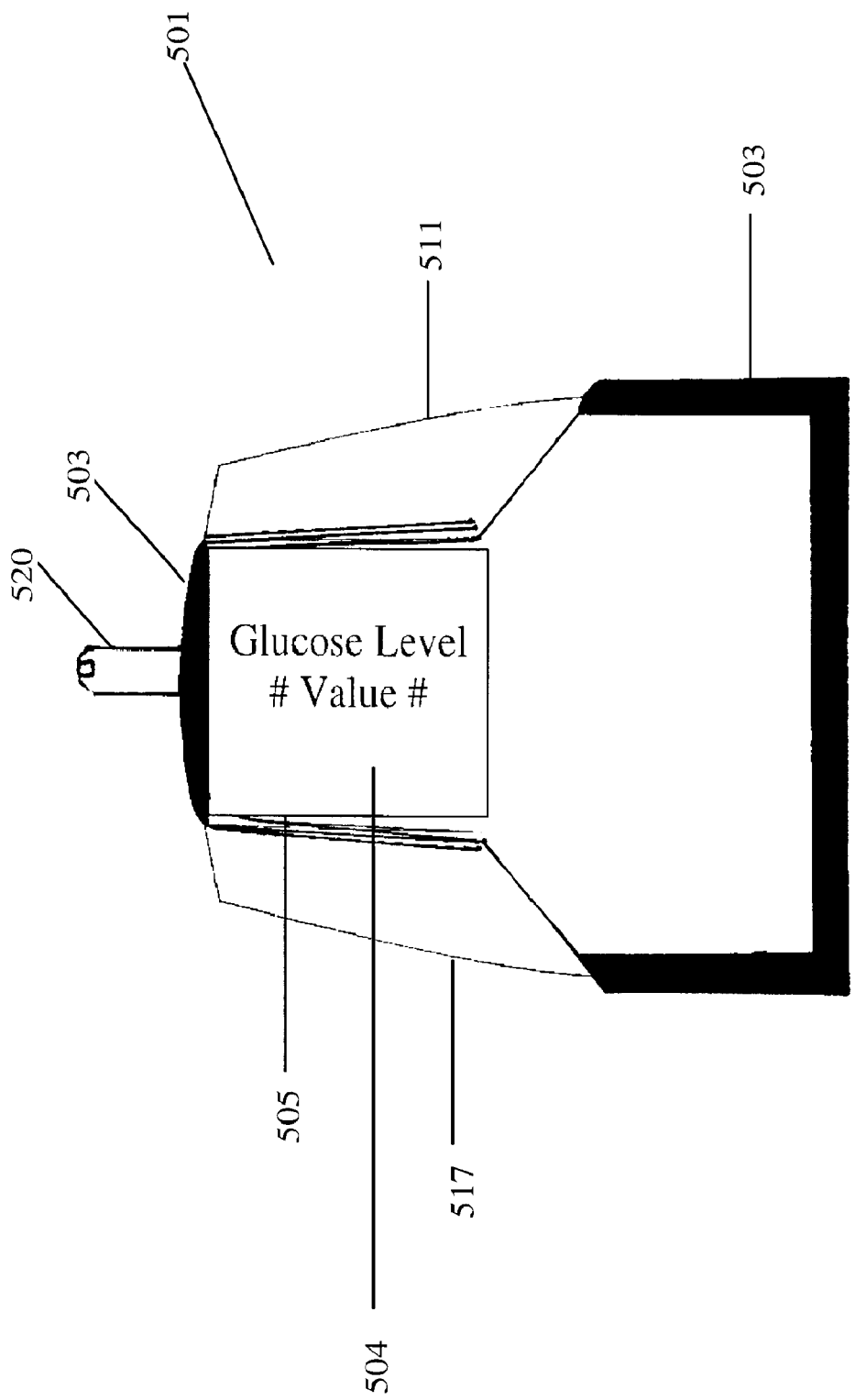
FIG. 5A is a top view of a combined lancing and meter device in accordance with an embodiment of the present invention.
Figure 5B:
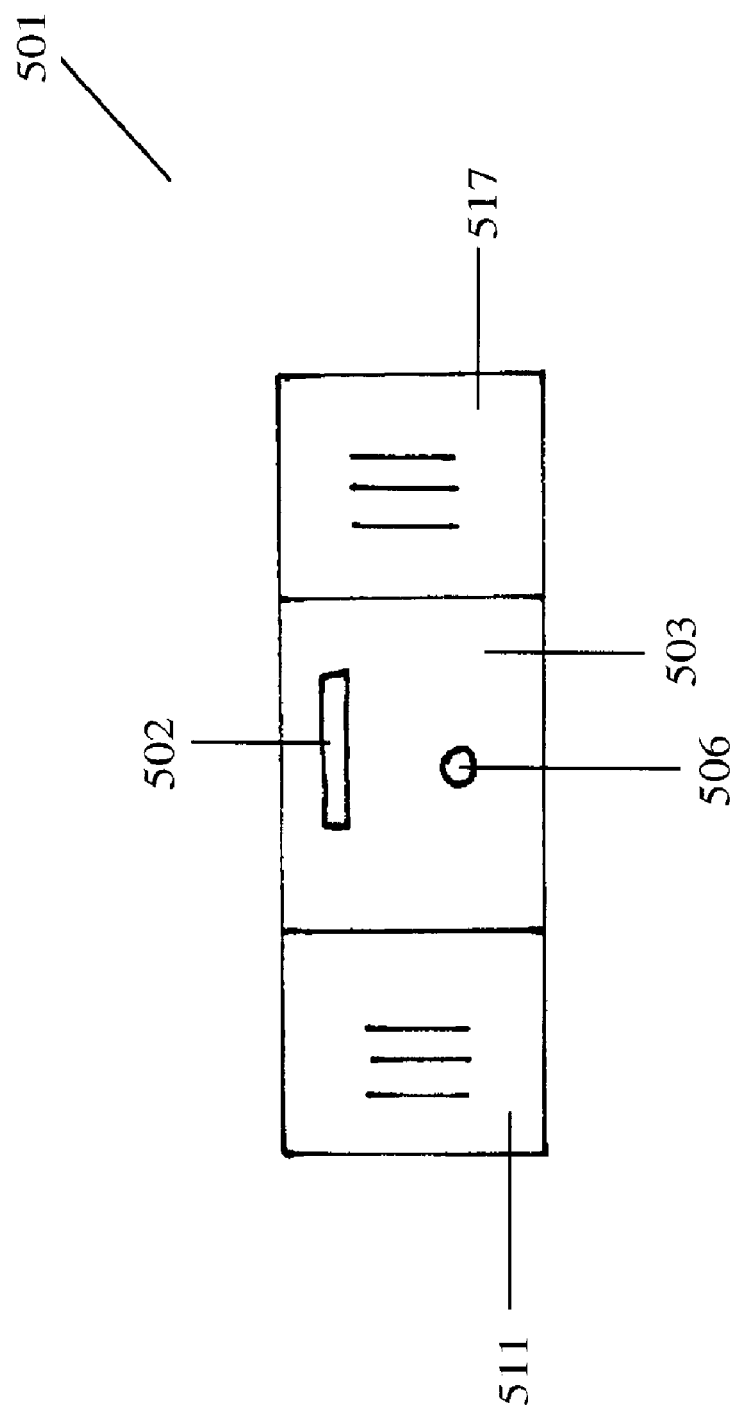
FIG. 5B is an end on first lancing end view of a combined lancing and meter device in accordance with an embodiment of the present invention.

FIGS. 5A and 5B illustrate a combined lancet and analyte meter 501 of the present invention having cantilevered priming arms 511, 517 for priming the lancet portion the device. The housing 503 of the combined device 501 has a test strip opening 502 sized to receive a test strip 520, a display opening 505 sized to receive a meter display 504, and a lancet opening 506 sized to receive a tissue penetrating portion of a lancet. The analyte meter comprises a test strip interface for receiving a test strip; a processor programmed to perform a diagnostic test on a sample applied to a test strip received in the test strip interface to determine a concentration of an analyte within the sample; and the meter display 504 for displaying the result of the analyte measurement to the user. In preferred embodiments the processor is programed to determine the concentration of glucose within a blood sample.

The invention claimed is:

1. A lancing device, for use with a lancet for lancing body tissue to result in a wound for bleeding, the lancing device comprising:
   (a) a housing having an internal channel extending within the housing from a first lancing end toward a second end of the housing;
   (b) a lancet carrier translationally mounted within the internal channel for carrying a lancet along a strike path of the lancet carrier, said strike path starting at a primed position toward the second end of the housing and extending to a lanced position at the first lancing end of the housing,
   (c) a lancet driver for storing energy and then driving the lancet carrier along the strike path from the primed position to the lanced position; and
   (d) a first cantilevered priming arm comprising a first arm portion that is generally parallel to the internal channel and a second arm portion that is generally perpendicular to the internal channel, wherein the second arm portion is connected to the lancet carrier,
wherein movement of the first arm portion toward the internal channel draws the lancet carrier to a primed position and stores energy in the lancet driver.

2. The device of claim 1, further comprising:
a second cantilevered priming arm comprising a first arm portion that is generally parallel to the internal channel and a second arm portion that is generally perpendicular to the internal channel, said first and second cantilevered priming arms being disposed on opposing sides of the internal channel, wherein movement of the first arm portions of the either or both of the first or second cantilevered arms toward the internal channel draws the lancet carrier to a primed position and stores energy in the lancet driver.

3. The device of claim 1, further comprising:
a shuttle disposed within the internal channel, wherein the shuttle connects the first cantilevered priming arm to the lancet carrier, said shuttle and lancet carrier comprising a protrusion and correspond depression that engage to draw the lancet carrier to a primed position and that release to fire the device.

4. The device of claim 3, further comprising:
a bump disposed on either of the shuttle or the housing and a track disposed on the other of the shuttle or the housing, said bump and said track engage to tip the shuttle as the lancet carrier is drawn to the primed position, such that after the lancet carrier reaches the primed position the protrusion and corresponding depression disengage thereby releasing energy stored in the lancet driver and firing the device.

5. The device of claim 4, further comprising:
a shuttle return spring compressed by the shuttle when the lancet carrier is in the primed position, said shuttle return spring drives the cantilever arms to a resting position and drives the shuttle along the strike path toward the lancet carrier located in a resting position to engage the protrusion and corresponding depression upon release of the cantilevered priming arm.

6. The device of claim 1, further comprising:
a lancet carrier return spring that interacts with the lancet carrier to return the lancet carrier to a resting position within the internal channel after the device is fired.

7. The device of claim 1, further comprising a lancet disposed within the lancet carrier.

8. The device of claim 1, further comprising:
(e) a second cantilevered priming arm comprising a first arm portion that is generally parallel to the internal channel and a second arm portion that is generally perpendicular to the internal channel, said first and second cantilevered priming arms being disposed on opposing sides of the internal channel,
(f) a shuttle disposed within the internal channel, wherein the shuttle connects the first and second cantilevered priming arms to the lancet carrier, said shuttle and lancet carrier comprising a protrusion and correspond depression that engage to draw the lancet carrier to a primed position and that release to fire the device,
(g) a bump disposed on either of the shuttle or the housing and a track disposed on the other of the shuttle or the housing, said bump and said track engage to tip the shuttle as the lancet carrier is drawn to the primed position, such that after the lancet carrier reaches the primed position the protrusion and corresponding depression disengage thereby releasing energy stored in the lancet driver and firing the device,
(h) a lancet carrier return spring that interacts with the lancet carrier to return the lancet carrier to a resting position within the internal channel after the device is fired,
(i) a shuttle return spring compressed by the shuttle when the lancet carrier is drawn toward the primed position, said shuttle return spring drives the cantilever arms to a resting position and drives the shuttle along the strike path toward the lancet carrier located in a resting position to engage the protrusion and corresponding depression upon release of the cantilevered priming arms, and
(j) a lancet disposed within the lancet carrier,
wherein movement of the first arm portions of the first, the second, or both the first and the second cantilever priming arms draws the lancet carrier toward the primed position and stores energy in the lancet driver.

9. The device of claim 1, wherein:
the housing has a test strip opening sized to receive a test strip and a display opening sized to receive a meter display,
the device further comprising:
an analyte meter disposed within the housing, the analyte meter comprising: a test strip interface for receiving a test strip; a processor programmed to perform a diagnostic test on a sample applied to a test strip received in the test strip interface to determine a concentration of an analyte within the sample; and the meter display for displaying the result of the analyte measurement to the user.

10. The device of claim 9, wherein the processor is programmed to determine the amount of glucose in a sample.

11. The device of claim 1, further comprising:
a firing ramp disposed within the internal channel at a position wherein the firing ramp and the second arm portion of the first cantilevered priming arm interact as the lancet carrier is drawn to a primed position, said interaction to disengage the connection between the second portion of the priming arm and the lancet carrier when the lancet carrier has reached the primed position thereby releasing energy stored in the lancet driver and firing the device.

12. The device of claim 11, further comprising:
a cantilevered arm return spring that biases the cantilevered arm toward a resting position away from the internal channel.

13. The device of claim 1, wherein upon movement of the first arm portion toward the internal channel energy is translated into movement of the second arm portion that draws the lancet carrier along the strike path toward the primed position.

14. The device of claim 1, wherein the first arm portion is connected to the lancet carrier through the second arm portion.

15. The lancing device of claim 1, wherein a portion of the first arm portion is disposed exterior to the housing.

16. The lancing device of claim 1, wherein the first cantilevered priming arm is a single piece construction wherein the first and second arm portions are fixed with respect to each other.

17. A lancing device, for use with a lancet for lancing body tissue to result in a wound for bleeding, the lancing device comprising:
(a) a housing having an internal channel extending within the housing from a first lancing end toward a second end of the housing;
(b) a lancet carrier translationally mounted within the internal channel for carrying a lancet along a strike path of the lancet carrier, said strike path starting at a primed position toward the second end of the housing and extending to a lanced position at the first lancing end of the housing,
(c) a lancet driver for storing energy and then driving the lancet carrier along the strike path from the primed position to the lanced position; and
(d) a first cantilevered priming arm comprising a first arm portion that is generally parallel to the internal channel and a second arm portion that is generally perpendicular to the internal channel, wherein the second arm portion is connected to the lancet carrier,
(e) a second cantilevered priming arm comprising a first arm portion that is generally parallel to the internal channel and a second arm portion that is generally perpendicular to the internal channel,
wherein said first and second cantilevered priming arms are disposed on opposing sides of the internal channel, wherein movement of the first arm portion of the either or both of the first or second cantilevered arms toward the internal channel draws the lancet carrier to a primed position and stores energy in the lancet driver, and
(f) a pair of firing ramps disposed within the internal channel at a position wherein the firing ramps and the second arm portions of the cantilevered priming arms respectively interact as the lancet carrier is drawn to a primed position, said respective interaction to disengage the connection between the second arm portion of the respective priming arm and the lancet carrier when the lancet carrier has reached the primed position thereby releasing energy stored in the lancet driver and firing the device.

18. The device of claim 17, further comprising:

a pair cantilevered arm return springs that respectively bias the cantilevered arms toward a resting position away from the internal channel.

19. The device of claim 17, wherein the lancet driver is a coiled spring.

20. In a lancing device having a housing, an internal channel extending within the housing, a lancet carrier disposed in the internal channel, and a lancet driver, wherein a user applies force to a housing to prime that lancet carrier into a primed position, the improvement comprising:

a cantilevered priming arm comprising a first arm portion that is generally parallel to the internal channel and a second arm portion that is generally perpendicular to the internal channel, wherein the second arm portion is connected to the lancet carrier, wherein movement of the first arm portion toward the internal channel draws the lancet carrier to a primed position and stores energy in the lancet driver.

21. The improved device of claim 20, further comprising:

a second cantilevered priming arm comprising a first arm portion that is generally parallel to the internal channel and a second arm portion that is generally perpendicular to the internal channel, said first and second cantilevered priming arms being disposed on opposing sides of the internal channel, wherein movement of the first arm portions of the either or both of the first or second cantilevered arms toward the internal channel draws the lancet carrier to a primed position and stores energy in the lancet driver.

* * * * *